(12) United States Patent
Jeong et al.

(10) Patent No.: US 10,131,868 B2
(45) Date of Patent: Nov. 20, 2018

(54) DEVICES, SYSTEMS AND METHODS FOR AUTOMATED CELL CULTURING

(71) Applicant: General Electric Company, Schenectady, NY (US)

(72) Inventors: Younkoo Jeong, Niskayuna, NY (US); Weston Blaine Griffin, Niskayuna, NY (US); Vandana Keskar, Niskayuna, NY (US); Zhipeng Zhang, Cupertino, CA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 107 days.

(21) Appl. No.: 15/376,259

(22) Filed: Dec. 12, 2016

(65) Prior Publication Data
US 2017/0088810 A1  Mar. 30, 2017

Related U.S. Application Data

(62) Division of application No. 14/499,709, filed on Sep. 29, 2014, now Pat. No. 9,550,972.

(51) Int. Cl.
| | |
|---|---|
| *C12M 1/00* | (2006.01) |
| *C12M 1/02* | (2006.01) |
| *C12M 1/04* | (2006.01) |
| *C12M 1/34* | (2006.01) |

(52) U.S. Cl.
CPC ............ *C12M 41/14* (2013.01); *C12M 23/02* (2013.01); *C12M 23/24* (2013.01); *C12M 29/00* (2013.01); *C12M 41/22* (2013.01); *C12M 41/26* (2013.01); *C12M 41/34* (2013.01)

(58) Field of Classification Search
CPC ..................................................... C12M 23/02
See application file for complete search history.

(56) References Cited

U.S. PATENT DOCUMENTS

| | | |
|---|---|---|
| 3,910,172 A | 10/1975 | Jaegle |
| 5,320,963 A | 6/1994 | Knaack et al. |
| 5,599,703 A | 2/1997 | Davis et al. |
| 6,835,566 B2 | 12/2004 | Smith et al. |
| 6,953,692 B2 | 10/2005 | Heidemann et al. |
| 7,524,513 B2 | 4/2009 | Hai-Quan et al. |
| 8,114,664 B2 | 2/2012 | Weathers et al. |
| 8,828,337 B2 | 9/2014 | Kensy et al. |
| 2003/0119107 A1 | 6/2003 | Dang et al. |

(Continued)

OTHER PUBLICATIONS

G. Catapano et al., "Bioreactor Design and Scale-Up", Cell and Tissue Reaction Engineering Principles and Practice, 2009, Abstract—1 Page.

*Primary Examiner* — Rosanne Kosson
(74) *Attorney, Agent, or Firm* — GE Global Patent Operation; Pabitra Chakrabarti

(57) ABSTRACT

A bioreactor is provided. The bioreactor is a multi-scalable bioreactor, which comprises a culture vessel for seeding and culturing cells by adding a cell-culture media, wherein the culture vessel comprises at least a side wall and a bottom surface, a specific heat transfer area and a specific gas transfer area; wherein the culture vessel is configured to accommodate the cell-culture media volume up to 10 liters, and wherein the specific heat transfer area and the specific gas transfer area are independent of cell-culture media volume. A kit for culturing cells in a large scale is also provided which further comprises disposable tubings, culture bag or combinations thereof. A method for culturing cells is also provided.

19 Claims, 14 Drawing Sheets

(56) References Cited

U.S. PATENT DOCUMENTS

| | | |
|---|---|---|
| 2008/0032398 A1 | 2/2008 | Cannon et al. |
| 2009/0269849 A1 | 10/2009 | Lee et al. |
| 2010/0112700 A1 | 5/2010 | Shaaltiel et al. |
| 2012/0231500 A1 | 9/2012 | Daramola et al. |
| 2013/0288346 A1 | 10/2013 | Tuohey et al. |
| 2014/0004593 A1 | 1/2014 | Boldog et al. |

DEVICES, SYSTEMS AND METHODS FOR AUTOMATED CELL CULTURING

CROSS REFERENCE TO RELATED APPLICATIONS

This application is a division of U.S. patent application Ser. No. 14/499,709, filed Sep. 29, 2014, now copending, the entire disclosure of which is incorporated herein by reference.

FIELD

The invention generally relates to devices, systems and methods for seeding and culturing cells and more particularly to seeding and culturing cells using an automated cell seeding and culturing system configured to accommodate expandable media volume.

BACKGROUND

Cell culture technology has advanced significantly over the last few decades and has contributed immensely in therapeutic applications, clinical studies, pharmaceutical research and development, and the bioprocess industry by expanding various cell lines and synthesizing different biomolecules of interest. To meet an increasing demand of therapeutic protein candidates (such as monoclonal antibodies) or viable cells (such as mammalian cell lines) for therapeutic applications, large scale manufacturing facilities and high throughput technological developments for culturing large quantities of cells are highly desirable.

Bioreactors have long been practiced as the preferred scale-up method for cell expansion in bioprocess industry. Use of a seed train for cell expansion from a cryo-preserved inoculum is a significant process step to initiate a large-scale manufacturing campaign. For manufacturing biotherapeutics, maintaining a desired quality of cells or biomolecules is a key requirement. A seed train expansion is significant since the use of cryopreserved inoculum can directly be used for expansion of cells, which may ensure a desired quality.

In a typical seed train expansion process, cells are initially cultured from a cryopreserved small inoculum (e.g., 1-2 mL). The cryopreserved cells are thawed and seeded to culture vessels, such as T-flasks or spinner flasks and cultured by adding culture media under controlled incubation. To achieve a desired cell number, the cells are usually distributed in multiple culture vessels, followed by transferring to larger culture vessels with additional growth medium. The process of transferring cells into multiple vessels, adding growth medium and culturing cells are repeated until a determined cell mass is obtained for large scale production, and finally the cells are seeded to a bioreactor, such as Cellbag™ for WAVE Bioreactor™ or an Xcellerex™ for XDR stirred-tank bioreactor with single-use bag. However, the current seed train expansion process is disadvantageous as the process requires labor intensive and complex manual handling and generates a risk of contamination when using multiple culture vessels and repeated inoculum transfer. In addition, the lack of control of different parameters, such as pH or dissolved oxygen during scale-up may result in batch-wise variation of cell expansion. Further, the existing process and the set-up for the seed train expansion from a cryo-preserved cell sample requires a well trained personnel.

In bioreactor, change in volume of a media in a bioreactor vessel introduces changes on internal parameters of a bioreactor, such as pH, DO or temperature, the change may be compensated by having a vessel geometry that compensates for media volume increase and thus a simple more robust controller can be used to maintain the system parameters. Due to large volume change, control performance of standard controllers, such as a proportional-integral-derivative (PID) controller may not be sufficient. Therefore, there is a need to develop a robust system and process for seed train expansion at different scales that provides an optimization of parameters and culture conditions that achieve requisite productivity and desired quality with minimum human intervention and ensures a smooth scale-up.

BRIEF DESCRIPTION

In one embodiment, a bioreactor is provided wherein the bioreactor comprises a culture vessel for seeding and culturing cells by adding a cell-culture media, wherein the culture vessel comprises at least a side wall and a bottom surface, a specific heat transfer area and a specific gas transfer area; wherein the culture vessel is configured to accommodate the cell-culture media volume upto 10 liters, and wherein the specific heat transfer area and the specific gas transfer area are constant and thereby independent of cell-culture media volume.

In another embodiment, a kit is provided, wherein the kit comprises one or more disposable tubings and a bioreactor comprising: a culture vessel for seeding and culturing cells by adding cells and a cell-culture media, wherein the culture vessel comprising at least a side wall and a bottom wall, is configured to accommodate the cell-culture media of a volume between 10 ml to 10 liter without introducing a significant change in bioreactor dynamics by maintaining a specific heat transfer area and a specific gas transfer area, wherein the specific heat transfer area and the specific gas transfer area are constant and thereby independent of cell-culture media volume; and the specific heat transfer area and a specific gas transfer area are defined by formula 1 & 2:

$$sHTA(h)=HTA(h)/V(h) \quad (1)$$

$$sGTA(h)=GTA(h)/V(h) \quad (2)$$

In yet another embodiment, a method for culturing cells comprises providing a bioreactor comprising: a culture vessel for seeding and culturing cells by adding cells and cell-culture media, wherein the culture vessel comprises at least a side wall and a bottom surface, a specific heat transfer area and a specific gas transfer area; and wherein the culture vessel is configured to accommodate the cell-culture media of a volume between 10 ml to 10 liter, and wherein the specific heat transfer area and the specific gas transfer area are constant and thereby independent of cell-culture media volume; seeding the cells to the culture vessel; adding a first volume of cell-culture media to the culture vessel; culturing the cells in the culture vessel to achieve a desired cell-density, and adding a second volume of cell-culture media for increasing the volume of the cell-culture media at a predetermined level to achieve a desired cell density, wherein the bioreactor dynamics remain minimally affected by maintaining the specific heat transfer area and the specific gas transfer area constant at different volumes of culture media.

DRAWINGS

These and other features, aspects, and advantages of the present disclosure will become better understood when the following detailed description is read with reference to the accompanying drawings in which like characters represent like parts throughout the drawings, wherein.

Figure 7:
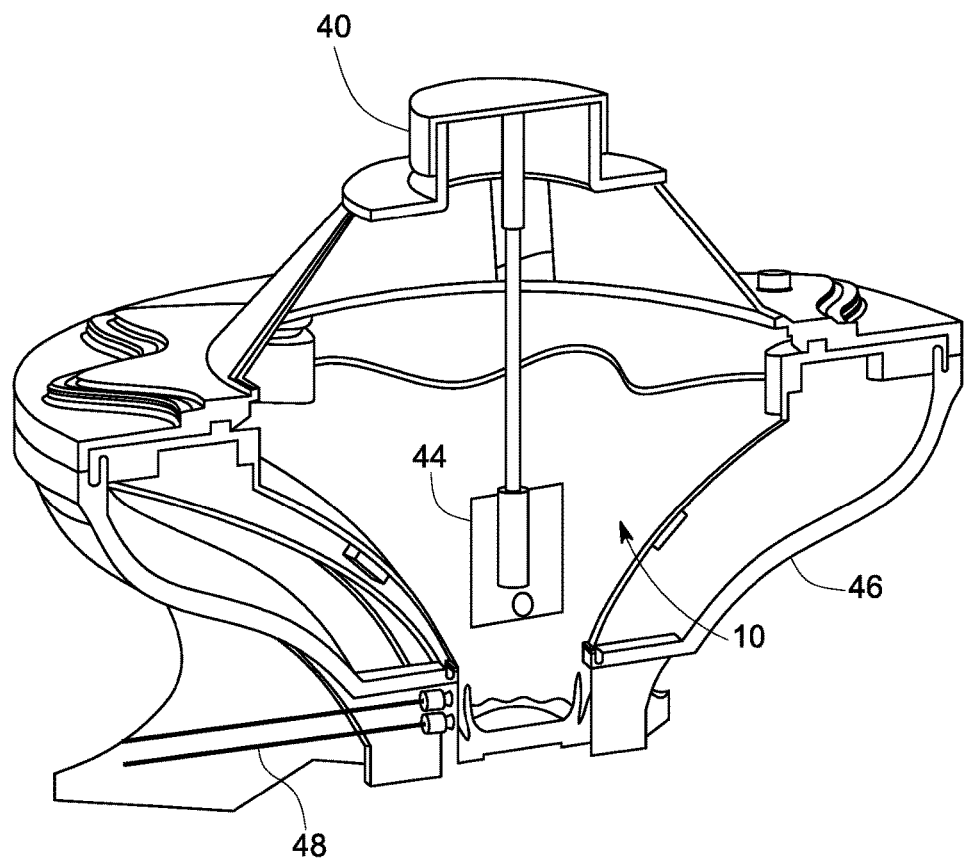
Figure 8B:
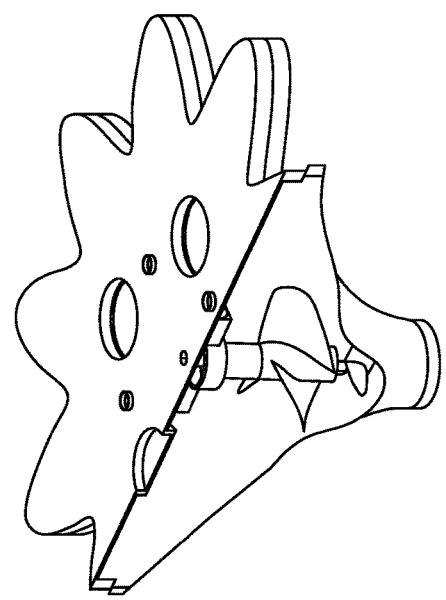
Figure 8C:
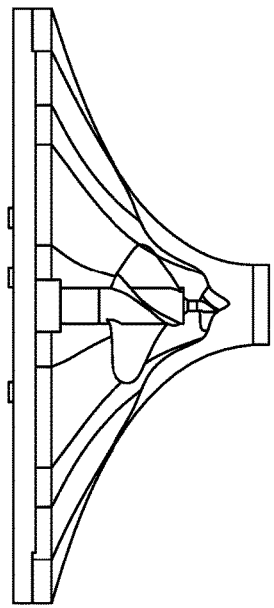
Figure 9:
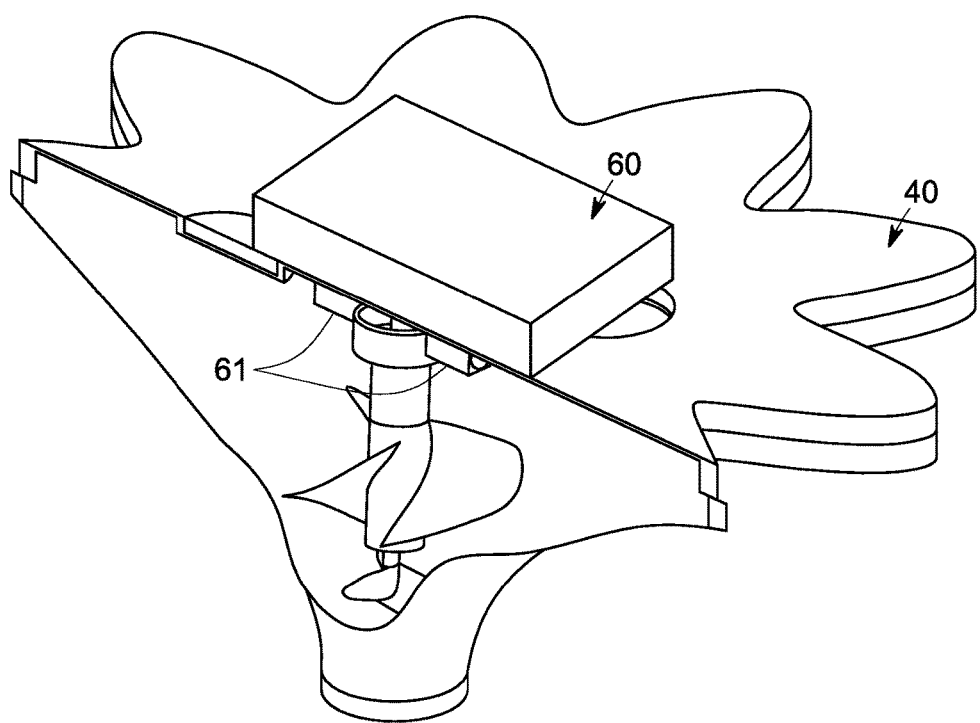
Figure 10:
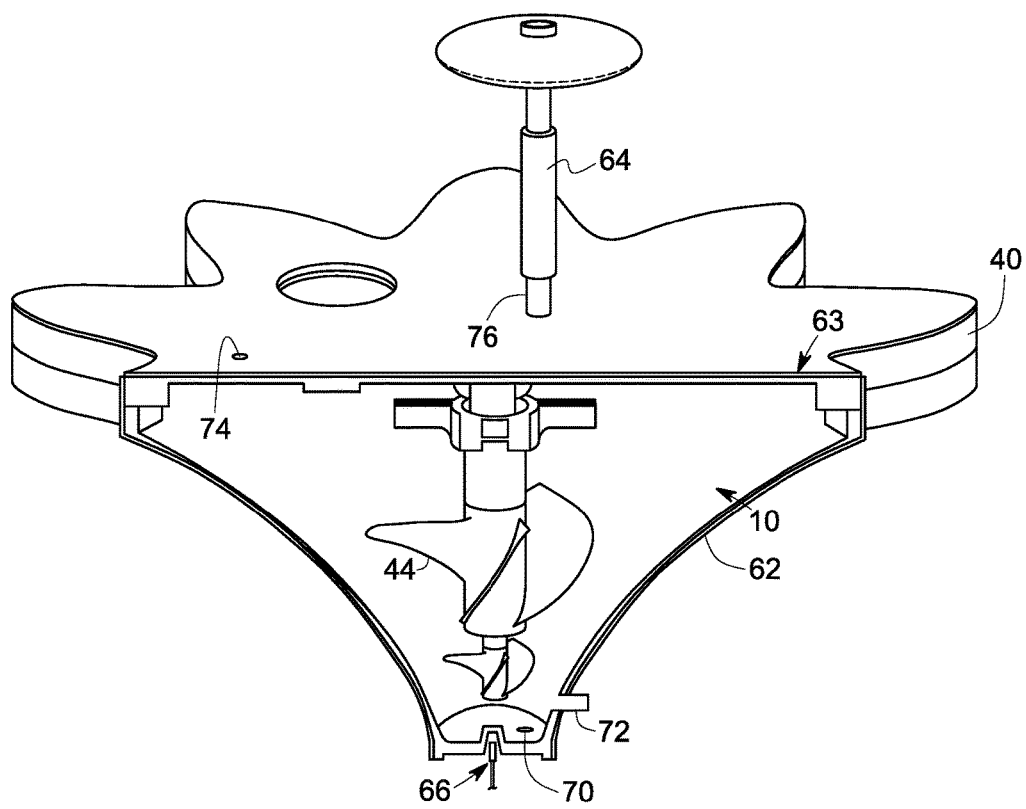
Figure 11:
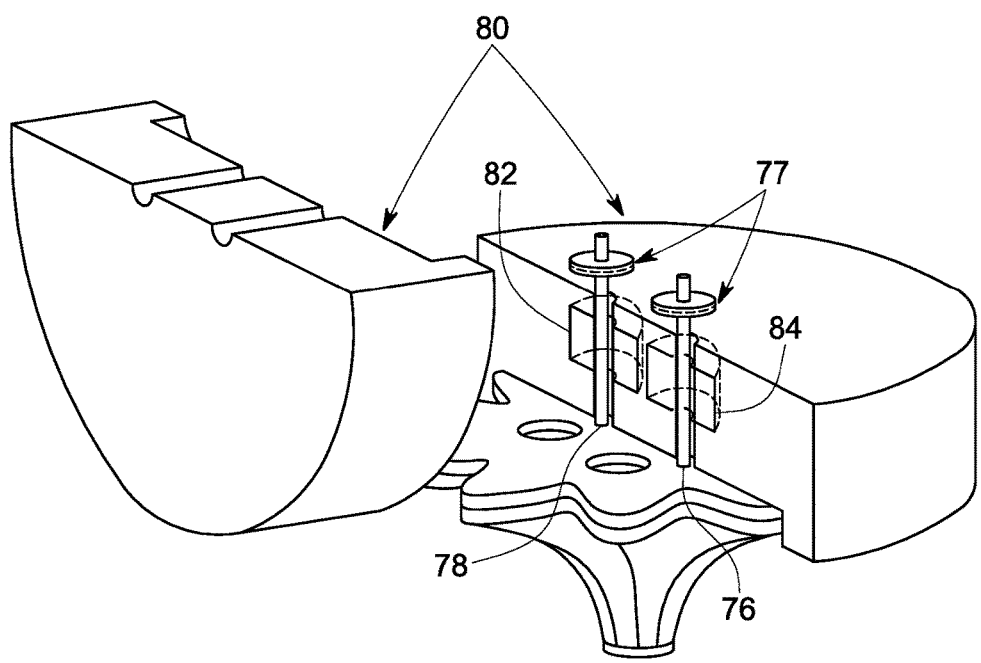
Figure 12:
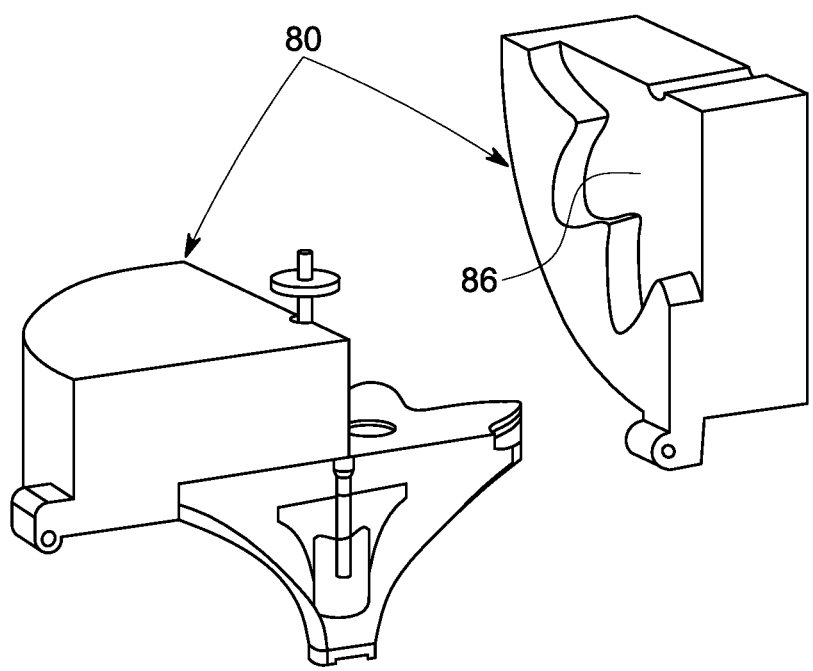
Figure 13:
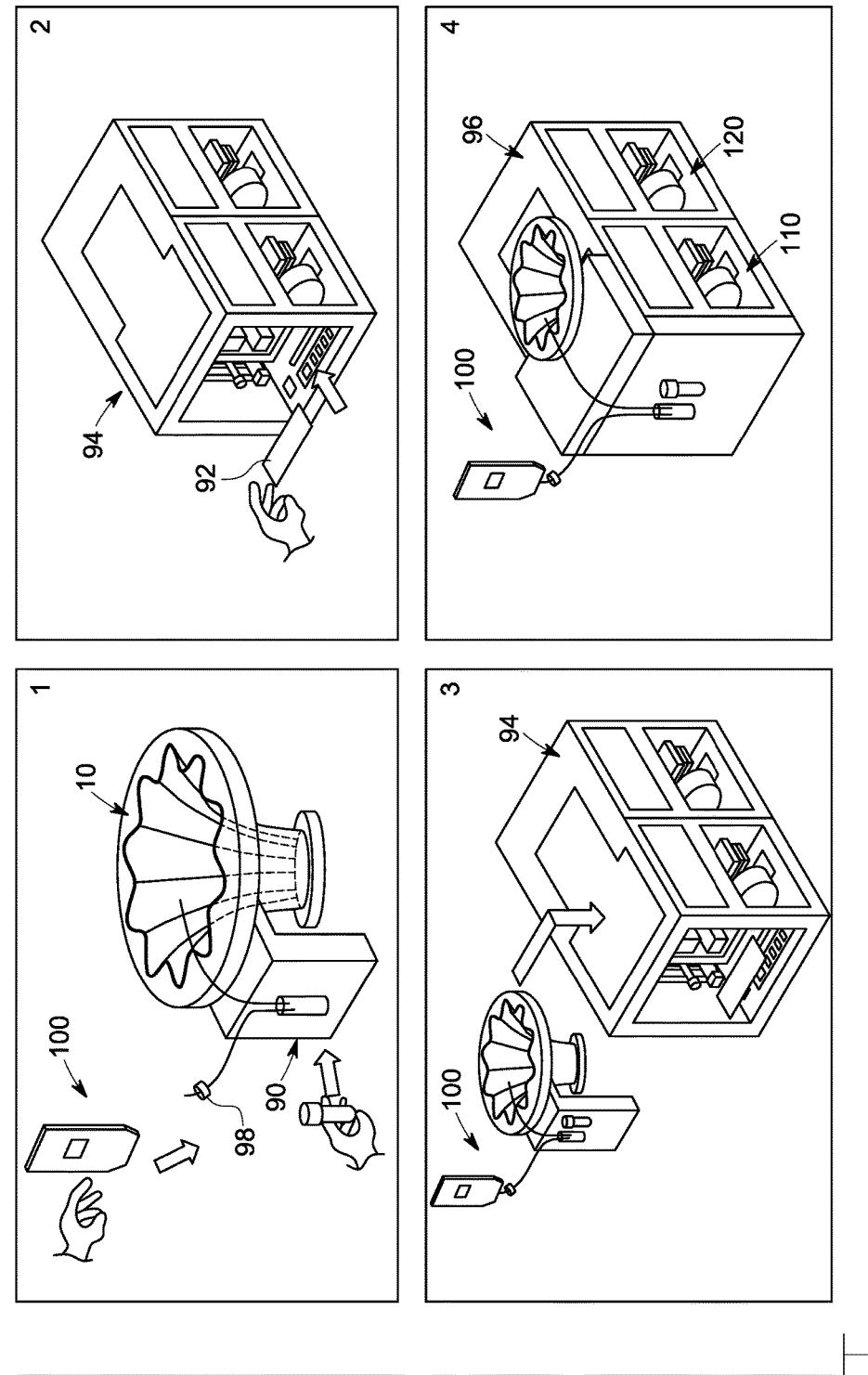
Figure 14:
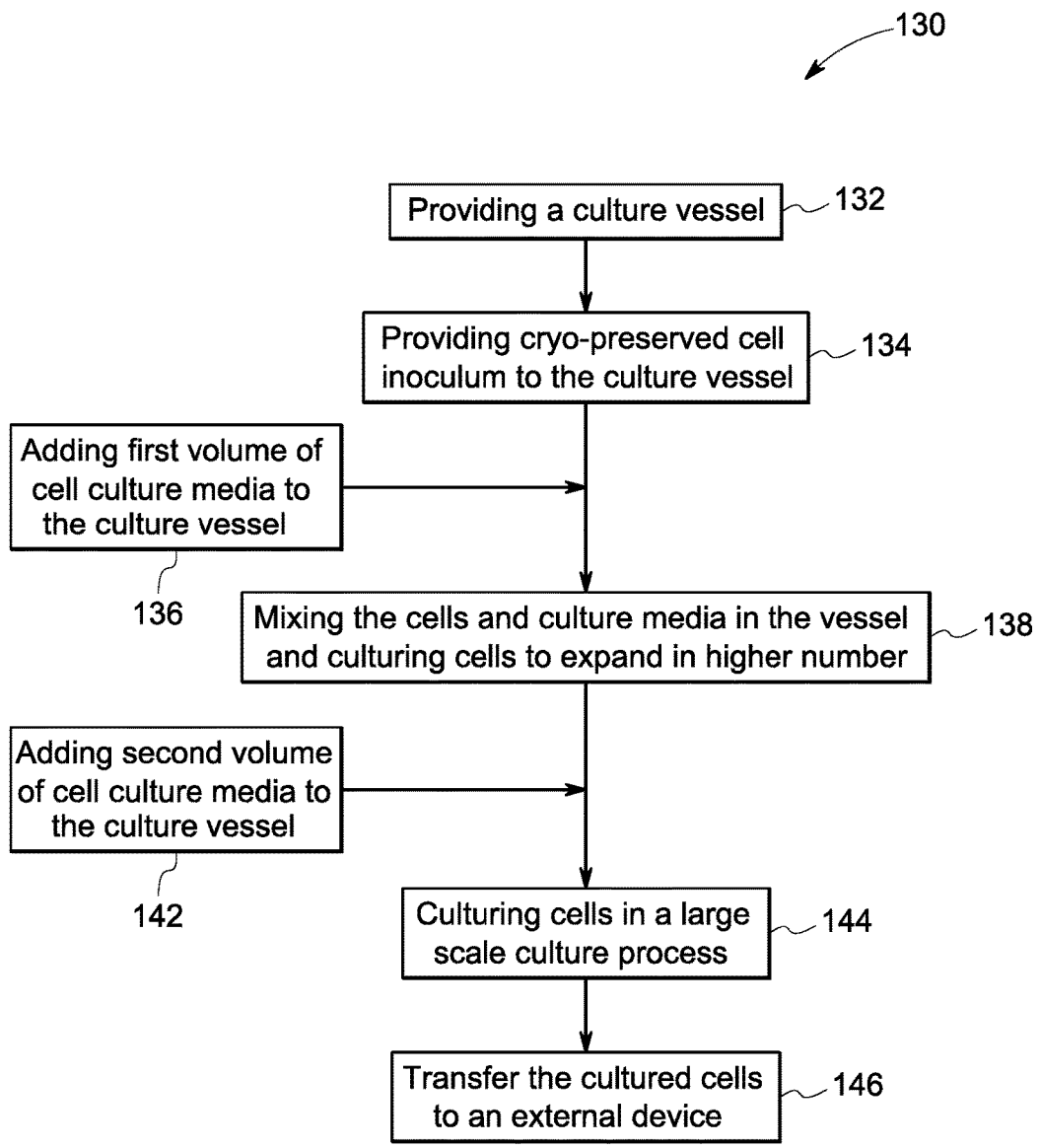

FIGS. 6 A and 6 B represent experimental graphs and theoretical graphs respectively, for time constant measurement of oxygen gas transfer ($\tau$) with a change in volume of the culture media in a culture vessel of cylindrical shape and flared shape with wavy wall (flower shape) design, in accordance with one embodiment of the present specification;

FIG. 7 is a cross-sectional view of a culture vessel design comprising a lid and different components, in accordance with one embodiment of the present specification;

FIG. 8 A is a schematic representation of a front view of an impeller used in a culture vessel, in accordance with one embodiment of the present specification;

FIG. 8 B is a cross sectional side view of a culture vessel comprising a centrally located impeller of FIG. 8 A, in accordance with one embodiment of the present specification;

FIG. 8 C is a cross sectional front view of a culture vessel comprising a centrally located impeller of FIG. 8 A, in accordance with one embodiment of the present specification;

FIG. 9 is a perspective view of a cell culture vessel with a lid comprising a magnetic agitator, a feeding port, a sampling port and a gas filter port, in accordance with aspects of the present specification;

FIG. 10 is a cross sectional side view of a culture vessel showing the positions of a centrally located impeller, sensors, a sampling path, a side heater, a noff-gas-condenser, a lid-heater, a magnetic agitator, in accordance with one embodiment of the present specification;

FIG. 11 is a perspective cross sectional view of a cell culture vessel with a two-door cover disposed on the lid of the vessel, in accordance with one embodiment of the present specification;

FIG. 12 is a perspective cross-sectional view of a cell culture vessel with a two-door cover disposed on the lid of the vessel, in accordance with one embodiment of the present specification;

FIG. 13 is a schematic representation of a method of assembling a bioreactor system, in accordance with one embodiment of the present technique;

FIG. 14 is a schematic representation of an exemplary flow chart of a method of seeding and culturing cells, in accordance with one embodiment of the present specification.

DETAILED DESCRIPTION

Embodiments of the present specification relate to devices, systems and methods for automated cell seeding and cell expansion starting from an inoculum. In certain embodiments, the automated cell expansion is achieved using a seed train expansion for cells. In some embodiments, devices, systems and methods for automated cell expansion may further include an automated inoculum transfer to a culture vessel, starting from cryo-preserved sample of cells. In one example, population of mammalian cells may be expanded using the devices, systems and methods of the present specification.

In one or more embodiments, a bioreactor is provided, wherein the bioreactor comprises a culture vessel for seeding and culturing cells by adding cells and a cell-culture media. The culture vessel may comprise at least a side wall and a bottom surface. The culture vessel is configured to accommodate the cell-culture media of a volume between 20 ml to 10 liter by maintaining a specific heat transfer area and a specific gas transfer area, wherein the specific heat transfer area and the specific gas transfer area are independent of cell-culture media volume.

Figure 1A:
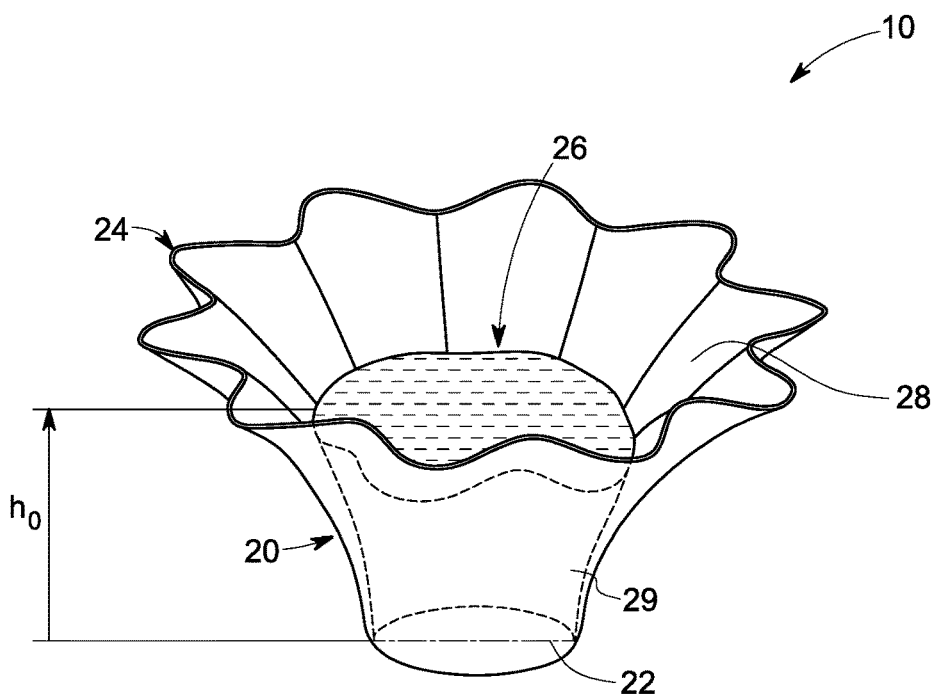
FIG. 1A is a schematic representation of a culture vessel, in accordance with one embodiment of the present specification.

The culture vessel may comprise a vessel or a container that is used for seeding cells followed by culturing the cells in the same vessel by adding culture media. As illustrated in FIG. 1A, one embodiment of the culture vessel 10 comprises at least a side wall 20 and a bottom surface 22. The vessel comprises a perimeter 24. The top surface area of the cell culture media may be referred to herein as a gas transfer area (GTA) 26 at height "$h_0$" of the vessel. The cell culture vessel may comprise an inner surface 28 and an outer surface 20. The surface area of the vessel, which is in contact with a culture media during cell culture, may be referred to herein as a heat transfer area (HTA) 29 at height "$h_0$".

The culture vessel may be designed to accommodate significant changes in media volume in the vessel, which does not affect the bioreactor dynamics. The term, "bioreactor dynamics" describes how fast the internal parameters of a bioreactor change with respect to change in external parameters. For example, when the heating blanket temperature changes, the temperature of the medium present in the bioreactor vessel changes accordingly. Further, the bioreactor systems are complex engineering devices that need to control multiple parameters in order to maintain an environment conducive to cell growth. The significant parameters for cell culture include pH, dissolved oxygen (DO), temperature, mixing/agitating speed and time constants.

As noted, in some embodiments, the culture vessel may be designed to accommodate significant changes in cell culture media volume without introducing a significant change in the bioreactor dynamics. For example, the culture vessel may accommodate about 1000× volume increase without introducing a significant change in the bioreactor dynamics. As noted, the culture vessel may be configured to accommodate the cell-culture media of a volume between 1 ml to 100 liter. In some embodiments, the culture vessel is configured to accommodate the cell-culture media of a volume between 10 ml to 10 liter. In some embodiments, the culture vessel is configured to accommodate a cell-culture media volume between 20 ml to 5 liter. In some other embodiments, the culture vessel is configured to accommodate a cell-culture media volume between 50 ml to 1.5 L. In these embodiments, the bioreactor dynamics may be maintained constant or near constant in spite of volume change in the culture vessel by maintaining a constant or near constant specific heat transfer area and specific gas transfer area.

The "multi-scale" or "multi-scalable" bioreactor is defined as a bioreactor whose specific heat transfer area and specific gas transfer area are constant or near constant, thereby invariant to volume change. The multi-scale bioreactor may be used to grow cells over various volume ranges unlike the reactors which typically require multiple vessels designed for different volume ranges to create an optimal or near-optimal cell growth environment. The bioreactor may be interchangeably referred to herein as a seed train bioreactor or multi-scalable bioreactor, which refers to a bioreactor that accommodates a range of volumes of culture media without affecting a specific heat transfer area and a specific gas transfer area of the culture vessel. The multi-scalable bioreactor eliminates the usage of multiple containers for multiple passages, such as cell culture-flasks or roller bottles during the seed train process and simplifies the process. The bioreactor allows scaling up of the culture media, when a large scale cell culture is required. In some embodiments, the culture vessel is configured to accommodate an expandable cell-culture media volume, wherein the vessel allows expanding the volume of the culture media, by adding a media multiple times or continuously, depending on the process requirement without affecting a specific heat transfer area and a specific gas transfer area. For example, the cell seeding may start with 10 ml of culture media with cells, and the media volume may be increased to 50 ml, 100 ml, 500 ml, 1 liter or 10 liter for scale up the culture media to grow large quantity of cells. In another example, the cell seeding may start with 50 mL of culture media with cells and the media may be increase from 50 mL to 100 mL, 200 mL, 400 mL, 800 mL, and 1.6 L. In these examples, the cell seeding may start with 50 mL of culture media with the cells and the media volume may be increased to double with respect to the starting media volume or scale up the culture media when the number of cells also increases to double. When the cell number increases to double, proportionally (may be 2×) adding media to the increased number of cells, the cell density is adjusted to same starting cell density. This step may be repeated for one or more times to scale up the culture to grow large quantities of cells. The specific heat transfer area and the specific gas transfer area may be constant and thereby independent of cell-culture media volume for the above examples.

The gas transfer area, GTA, is defined as the top surface area of the culture media present in the culture vessel when the total media volume is 'V'. The top surface area of the media is in contact with the mixed gas and able to exchange gas through the top surface area. The GTA may vary with the media volume (V). The specific gas transfer area, sGTA is defined as a ratio of the gas transfer area (GTA) and the total culture media volume (V). The specific gas transfer area affects the gas transfer dynamics, and thus pH and dissolved oxygen (DO) regulation dynamics in a bioreactor, since pH and DO are controlled through $CO_2$ and $O_2$ gas transfer from the bioreactor headspace to the cell-culture media.

The heat transfer area, HTA, is defined as a contact area of the vessel with media through which the heat flux flows into the culture media of the vessel or the heat flux flows out from the culture media to outside of the vessel. If a heating blanket is employed to heat the vessel and/or medium, the side surface area or side wall of the vessel which is in contact with the media at the volume 'V' is the HTA. HTA may vary as the media volume (V) varies. The specific heat transfer area, sHTA is defined as a ratio of the heat transfer area (HTA) and the total media volume (V). The specific heat transfer area affects the heat transfer dynamics, and thus may affect temperature regulation dynamics in a bioreactor.

The multi-scalable bioreactor may be designed to maintain two parameters constant at different volumes: specific heat transfer area and specific gas transfer area. As noted, sGTA and sHTA are defined as, GTA/V and HTA/V, respectively. In one or more embodiments, the specific heat transfer area may be represented by equation 1 and the specific gas transfer area may be represented by equation 2

$$\text{sHTA}(h)=\text{HTA}(h)/V(h) \tag{1}$$

$$\text{sGTA}(h)=\text{GTA}(h)/V(h) \tag{2};$$

The sGTA and sHTA are significant parameters, which may determine the time required by a dynamic system to respond to a given change of gas supply, cell culture metabolite production, and heater temperature, and environmental temperature. A vessel may be designed to have a constant sGTA and sHTA at various media volumes or for a range of media volumes; wherein the dynamic characteristics of the vessel may be invariant during the period of operation, which makes the system simple and consistent.

If the gas transfer area is defined as a function of the media height 'h', GTA(h), the media volume 'V' may be represented as:

$$V(h)=\int_0^h \text{GTA}(h)dh$$

Using the definition of specific gas transfer area:

$$\text{sGTA}(h)=\text{GTA}(h)/V(h)$$

$$\text{or, sGTA}(h)=\text{GTA}(h)/\int_0^h \text{GTA}(h)dh$$

Figure 1B:
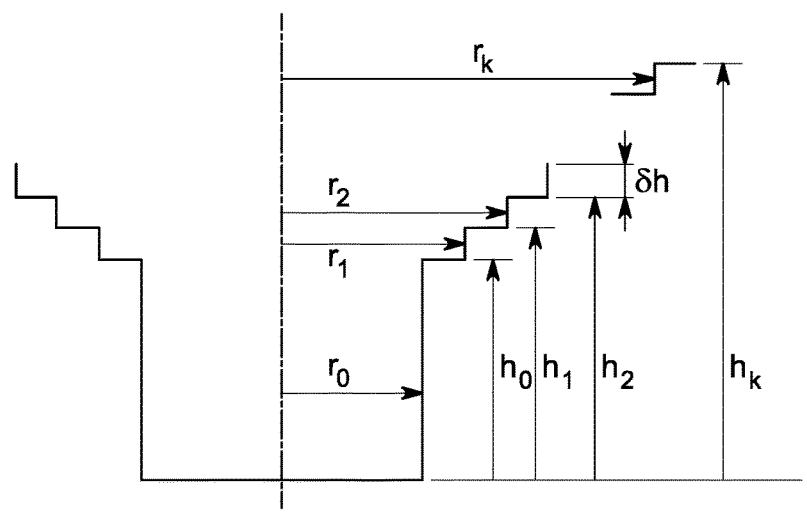
FIG. 1B is a schematic representation of a discretized culture vessel design, in accordance with one embodiment of the present specification.

If the perimeter of the vessel is defined as P(h) (as shown in FIG. 1 A), and the angle between the side wall of the vessel in contact with the medium and the gas transfer surface (or the liquid surface) at height 'h' is defined as $\theta_h$, the heat transfer area up to the height 'h' may be represented as:

$$HTA(h) = \int_0^h P(h)ds = \int_0^h \frac{P(h)}{\sin(\theta_h)} dh$$

Using the above definitions, the specific heat transfer area:

$$sHTA(h) = \left\{ \int_0^h \frac{P(h)}{\sin(\theta_h)} dh \right\} \Big/ \int_0^h GTA(h)dh$$

A vessel may be designed to meet the requirements such that sGTA(h) and sHTA(h) are constant or near constant over a range of volumes larger than an initial volume in order to make the process volume independent, which may include the design of GTA(h) and P(h). The initial volume has a non-zero height and it determines the target value for sGTA and sHTA. If a wave function, such as a sinusoidal wave is super positioned onto P(h), it is periodic in the space domain and whose summation of the area for a period is zero, it may be possible to design GTA(h) and P(h), independently. The ability to independently add a wave function to the perimeter of the of the vessel without changing the GTA or sGTA is advantageous because it provides the ability to then independently increase or decrease the HTA or sHTA without affecting the GTA or sGTA. Thus, the vessel shape may be changed to change sGTA or sHTA separately, however, changing both sGTA or sHTA may not be possible. As increase in one parameter often results in decrease of another parameter, a design of the vessel may be adopted such that multiple parameters may be designed independently, without sacrificing performances of the bioreactor system.

GTA(h) and P(h) may be designed such that sGTA and sHTA remain constant for height h, at any interval (0, infinity). Three steps were used to design such a vessel with constant sGTA and sHTA, which are illustrated below.

In a first exemplary step, a design of gas transfer area of GTA at height h is determined. Referring to FIG. 1 A, a design of GTA(h) at height "$h_0$" may be used to compute the sGTA(h0) or $sGTA(h_0) = GTA(h_0)/\int_0^{h_0} GTA(h)dh$. The computed sGTA at $h_0$ may represent the target value for the sGTA over the desired range of heights [$h_0$, h_max], wherein h_max represents the maximum height possible for the vessel. The vessel may have some initial finite volume of liquid in order to compute a GTA or sGTA, and the selected value for sGTA may represent a value that supports a desired cell culture dynamics independent of volume and thus may be used for all vessel volumes. In some embodiments, the vessel geometry may be designed such that the specific gas transfer area may be in the range of 0.2-0.8 $cm^{-1}$. In a non-limiting example, wherein the base function describing the cross-sectional area at different heights, on the interval [$h_0$, h_max] has a circular geometry with different radii, with a cross-section shown in FIG. 1 B. The radius at a given height h may be determined to ensure the sGTA is constant or near constant for each discrete location associated with a given radius and height. Thus, if a sufficient number of discrete height points are used to determine the circular cross-section over the desired height range, and the computed sGTA for each height is held constant, then the sGTA may also be constant or near constant for the given volume range associated with the height range of interest. Further, a continuous analytical function describing the radius of a circular cross-section that is dependent on the height may also be derived. The analytical function specifically provides a constant sGTA value for height h on the interval [$h_0$, h_max]. Thus at the first design step, the geometry of the vessel is determined over the height range of interest such that the sGTA is constant and near constant.

In the second design step, the design of perimeter P(h) at the height 'h' (FIG. 1 A) to maintains HTA or $$\left\{ \int_0^h \frac{P(h)}{\sin(\theta_h)} dh \right\} \Big/ \int_0^h GTA(h) dh$$

a constant is determined. In some embodiments, the vessel geometry may be designed such that the specific heat transfer area may be in the range of 0.4-1.2 $cm^{-1}$. Those skilled in the art will appreciate the fact that a simple cylindrical-walled vessel, where P (h) is defined as 2*pi*r for height h and $\theta_h$ is equal to 90° for height h, has a constant sHTA for height h, wherein height h represents all possible height h, and thus the cylindrical-walled vessel has a constant sHTA for all possible volumes in the vessel. However, a vessel with simple cylindrical-walled geometry will have a computed sGTA of the form 1/h that decreases with an increase in volume.

Continuing the non-limiting example from the first design step, the radius of the circular cross-section geometry at the height 'h' (designed at the first example) gives a basic perimeter and perimeter function. The perimeter may be modified such a way that the cross-sectional area at a given height does not change but the length of the perimeter may increase or decrease relative to the basic perimeter at a given height. Further, the perimeter may increase or decrease as a function of the height of the vessel. If the cross-sectional area is not affected for all height h, then the computed sGTA for all heights may remain unchanged. The length or shape of the perimeter may be modified by overlaying a periodic function of a given frequency and the magnitude of the periodic function may be dependent on the height and thereby dependent on the volume in the vessel.

In the third design step, a three-dimensional shape of a culture vessel may be determined using the sGTA (h) from the first design step and P (h) from the second design step. The vessel design may be determined considering the vessel parameters sGTA and sHTA held at a constant value. More specifically, given a base function describing the cross-sectional area at different heights, on the interval [$h_0$, h_max], the shape of the vessel at different heights, on the interval [$h_0$, h_max], may be determined such that the sGTA is constant for liquid volumes at different heights on the interval [$h_0$, h_max]. Given the shape of the cross-section at different heights (either described with discrete points or with an analytical function), a modification to the perimeter (either described with discrete points or with an analytical function) may be determined such that the sHTA also remains constant for liquid volumes at different heights within the vessel on the interval [$h_0$, h_max]. In a continuation of the non-limiting example from the second design step, a sinusoidal function that has amplitude, which varies with the parameter h and has a constant frequency, may be multiplied to the function describing the circular perimeter. In one example embodiment, the height and width of the vessel is optimized to 4.5 inch and 14 inch respectively, with a side wall geometry that meets the design criteria of a constant sGTA and sHTA from all height h on the interval [$h_0$, h_max], as shown in FIG. 1A.

One skilled in the art will appreciate the fact that one could satisfy the design criteria of constant sGTA and sHTA at discrete points over the height of the vessel and over the perimeter of the vessel. Further, any function or approximation could be used between the discretized design points. However, in the limit (i.e., with enough discrete design points) the discretized designed vessel may be substantially similar to a vessel designed using the step described above.

The design of an invariant dynamic vessel may be determined, wherein the gas transfer area (GTA) and heat transfer area (HTA) of the vessel remain simultaneously constant for all volumes greater than the designed initial or starting volume. For the invariant dynamics of gas transfer and heat transfer, the parameters GTA(h) and P(h) may be determined such that the following parameters are constant for all volumes greater than the starting volume:

$$sGTA = \frac{GTA(h)}{V(h)} = \frac{GTA(h)}{\int_0^h GTA(h)dh} \text{ and} \quad 1)$$

$$sHTA = \frac{HTA(h)}{V(h)} \approx \frac{\int_0^h P(h)\sin^{-1}(\theta_h)dh}{\int_0^h GTA(h)dh} \quad 2)$$

The vessel may comprise a base of any possible shape, such as circular, triangular, square or rectangular. One skilled in the art will appreciate that a vessel may be designed to have a constant or near constant sGTA at discrete points within the volume range of interest. As additional points within the volume range may be added to the discretized shape, the shape of the vessel may be determined by the base function shape, a desired sGTA, and the initial volume. A function for the radius and the height such that both sGTA and sHTA are constant for a range of h on the bounds [h_min to h_max] where h_min is not equal to zero.

In one embodiment, given a circular geometry base function for the design of the vessel, the height may be represented by the function, $h_k = h_0 + k \cdot \delta h$ and the radius at height $h_k$ may be represented by the function, $$r_k = r_0 \cdot \left(\frac{h_0}{h_0 - \delta h}\right)^{k/2}.$$

The parameters $h_0$ and $r_0$ result in an initial or starting volume $V_0$, where $$V_0 = h_0 \cdot \pi \cdot r_0^2$$

wherein, the given initial volume as a given sGTA and sHTA. With the functions for hk and rk defined in this manner, sGTA and sHTA may be the same for any given liquid volume added to the initial liquid volume. Given hk and rk, the gas transfer area, media volume, heat transfer area, specific gas transfer area and specific heat transfer area are respectively:

$$GTA(h_k) = \pi \cdot r_k^2$$

$$V(h_k) = \pi \cdot r_0^2 \cdot h_0 + \sum_{i=1}^{i=k} \pi \cdot r_i^2 \delta h;$$

$$HTA(h_k) \approx 2\pi r_0 h_0 + \sum_{i=1}^{k} a_i \frac{\pi(r_i + r_{i-1})}{\cos\theta_i} \delta h,$$

$$sGTA = \frac{1}{h_0} \text{ and } sHTA = \frac{2}{r_0}.$$

Figure 2:
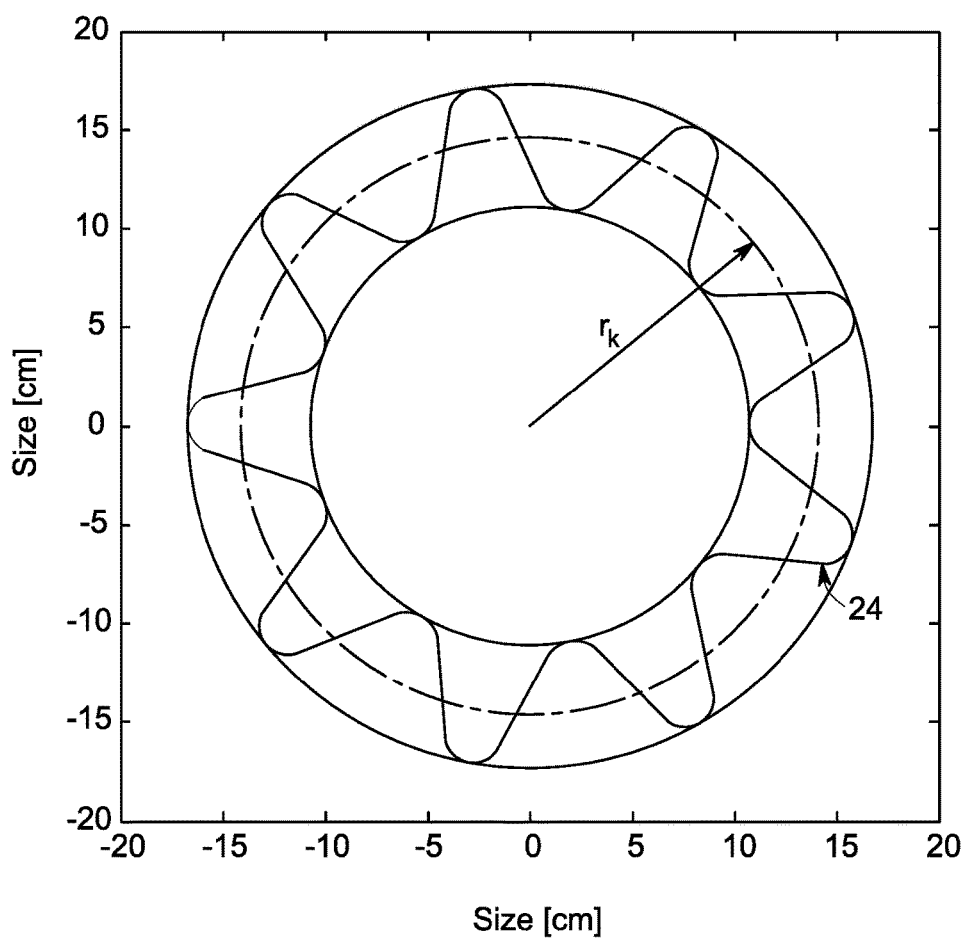
FIG. 2 is a schematic representation of a cross-sectional top view of a perimeter design, of a culture vessel, in accordance with one embodiment of the present specification.

In another example of the vessel design, the perimeter P (h) of the vessel may be configured such that it meets the invariant heat transfer dynamics requirement. The surface area of the vessel side wall to be used for heating is determined by the perimeter P(h) at height, h, for all h greater than $h_0$. In order to modify the perimeter such that the requirement for the invariant heat transfer dynamics to be met, any periodic function may be added to the side surface without disturbing the invariant gas transfer design as discussed above. One such periodic function applied to the perimeter P (h) is illustrated in FIG. 2.

In one embodiment, P(h) may be defined such that:

$$HTA(h_k) = \int_0^h \frac{P(h)}{\sin(\theta_h)} dh$$

$$\approx 2\pi r_0 h_0 + \sum_{i=1}^{k} a_i \frac{\pi(r_i + r_{i-1})}{\sin\theta_i} \delta h$$

Where $a_i$ is a scaling factor of perimeter at $i^{th}$ height and can be computed recursively.

$$\frac{HTA(h)}{V(h)} = \frac{HTA(h)}{\int_0^h GTA(h) dh} = \frac{2}{r_0} = sHTA,$$

wherein, the sHTA is considered as a constant.

The design of a multi-scalable bioreactor for cell seed-train expansion is determined using above calculations. The above calculations and functional form of hk, rk, and P(h), may lead to a flower-like shape of the culture vessel, as shown in FIG. 1A, with wavy perimeter 24 as shown in FIG. 2. Furthermore, a constant sGTA and sHTA may be simultaneously achieved for increased volume of liquid added to the vessel containing the initial liquid volume, filled to level $h_0$, which is present at the start of the process.

Figure 3:
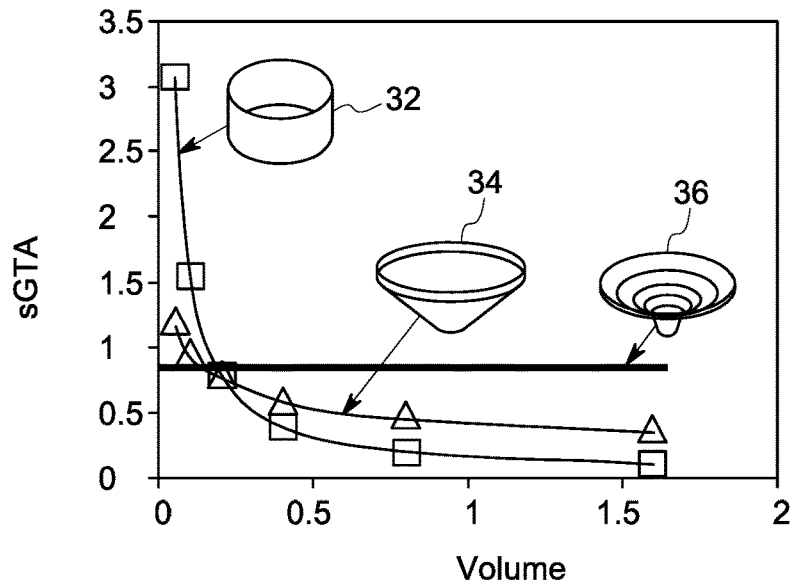
FIG. 3 represents graphs showing a change in specific gas transfer area with a change in volume of the liquid media using different culture vessels having a cylindrical shape, a conical shape or a flared shape, in accordance with one embodiment of the present specification.

Common culture vessels of different shapes may be used to illustrate the typical design constraints associated with trying to simultaneously achieve a volume independent specific gas transfer area and specific heat transfer area. According to the definition, the specific gas transfer area decreases with increasing volume for a cylindrical shaped culture vessel 32, as shown in FIG. 3, since the gas transfer area for the cylindrical vessel does not increase with increasing volume. In case of a conical shaped vessel 34, the specific gas transfer area always decreases with increasing volume (FIG. 3). For a flared shaped vessel 36, which is designed using the first design step described above, the specific gas transfer area remain constant with increasing volume (FIG. 3), since the gas transfer area for the flared shape vessel increases with increasing volume.

Figure 4:
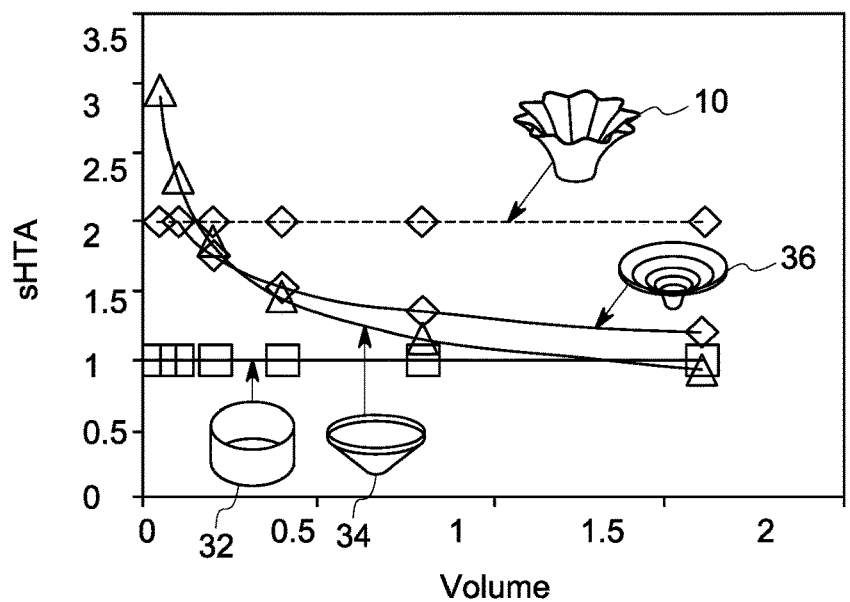
FIG. 4 represents graphs showing a change in specific heat transfer area with a change in volume of the liquid media in culture vessels having a cylindrical shape, a conical shape, a flared shape or a flared shape with wavy wall design (flower shape) in accordance with one embodiment of the present specification.

Common culture vessel shapes and the associated specific heat transfer area as a function of volume are also illustrated in FIG. 4. The specific heat transfer area for a flared opening vessel 36 decreases with volume, as shown in FIG. 4, since the heat transfer area for the flared shaped vessel does not increase in a same proportion with the increased volume. To make both the specific gas transfer area and specific heat transfer area constant with respect to a volume change, a wave feature design using the second design step described above, may be added onto the flared opening design 36 to provide additional heat transfer area without changing volume or gas transfer area. This may result in a flower-like shaped vessel 10 (FIG. 4), which is also shown in FIG. 1A. The design of flower shaped (flared shape with wavy wall design) culture vessel 10 (FIG. 1A and FIG. 4) yields an invariant specific gas transfer area and an invariant specific heat transfer area with respect to volume change. By maintaining invariant specific heat transfer area and specific gas transfer area in the design of the culture vessel, volume-invariant heat transfer and gas transfer dynamics are achieved at different volume scales.

Figure 5:
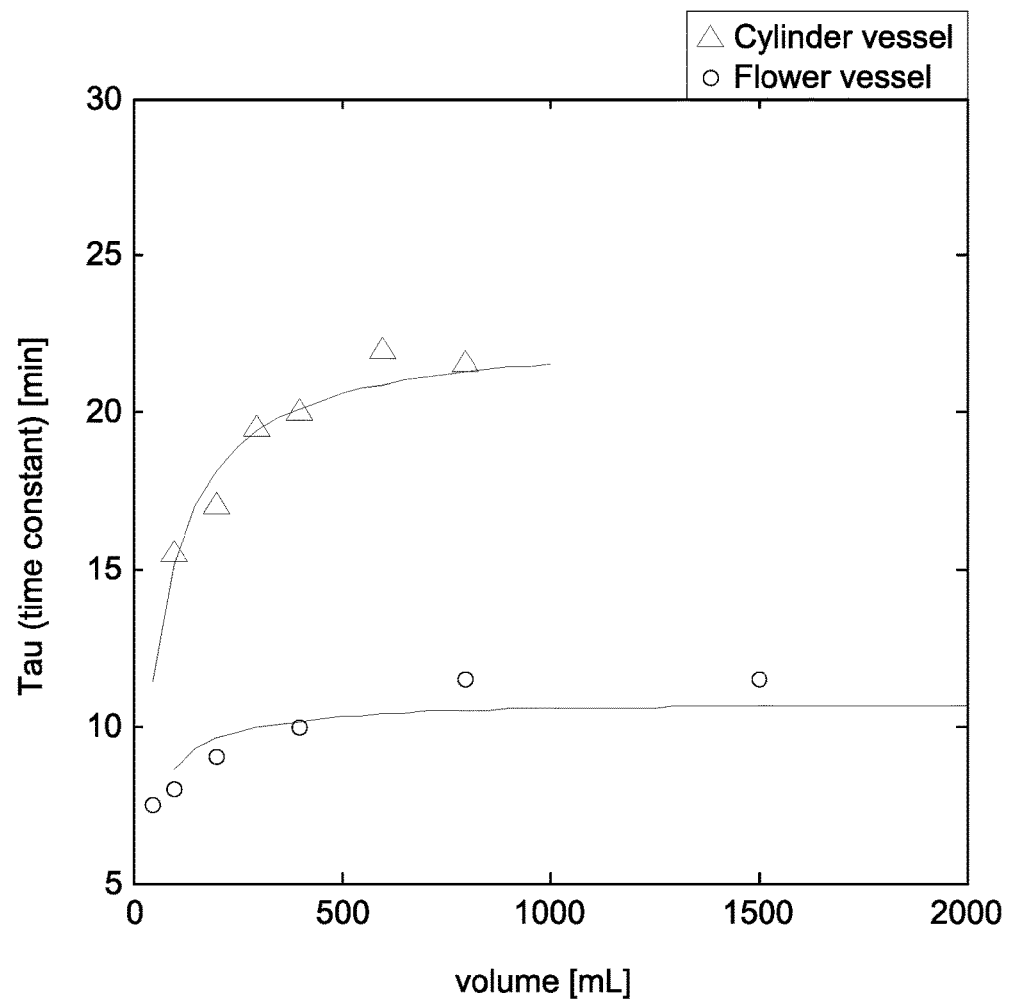
FIG. 5 represents graphs for a time constant measurement of heat transfer ($\tau$) with a change in volume of the culture media using a culture vessel of cylindrical shape and a vessel of flared shape with wavy wall (flower shape) design, in accordance with one embodiment of the present specification.

The flower shape 10 and cylindrical shape 32 vessels both have an invariant heat transfer dynamics associated with volume change, or more specifically, both have a constant sHTA for the volumes of interest, as shown in FIG. 4. Further, the heat transfer dynamics were measured for each of the designs of the vessel, by measuring the temperature change time constant τ, at different volumes. τ is near invariant for flower-shaped vessel, as shown in FIG. 5B, compared to a cylindrical vessel as shown in FIG. 5A. Slight decrease in τ at lower volumes (FIGS. 5A and 5B) was due to imperfect insulation resulting in heat loss at vessel bottom. As noted the time constant τ, which represents a time by which a particular system may respond to a change, typically equal to the time taken for a specified parameter to vary by a factor of 1-1/e (approximately 0.6321). In other words, the amount of time it takes a system to respond 63% of the step change.

Temperature (T), pH and dissolved oxygen (DO) may be considered as three significant environmental parameters for culturing cells in an automated seed train bioreactor. The specific gas transfer area is related to the gas transfer dynamics. The specific heat transfer area is related to the heat transfer dynamics. In some embodiments, the bioreactor is configured to maintain a set point for constant temperature, pH, dissolved oxygen or combinations thereof during operation. In some other embodiments, the set points for temperature, pH, and dissolved oxygen may be varied during the culturing process. The parameters, such as, temperature, pH, and dissolved oxygen may be actively controlled in the bioreactors.

The pH of the culture media may be controlled through $CO_2$ gas transfer from the culture media or to the culture media. In some embodiments, the bioreactor further comprises one or more pH sensors and/or dissolved oxygen sensors. In yet another embodiment, adding an acid or a base to the culture media of the culture vessel, the pH of the media may also be adjusted to a desired pH value. The cell culture process yields are typically maximum at an optimum pH, which is desirable to maintain during cell seeding and cell culture.

Figure 6A:
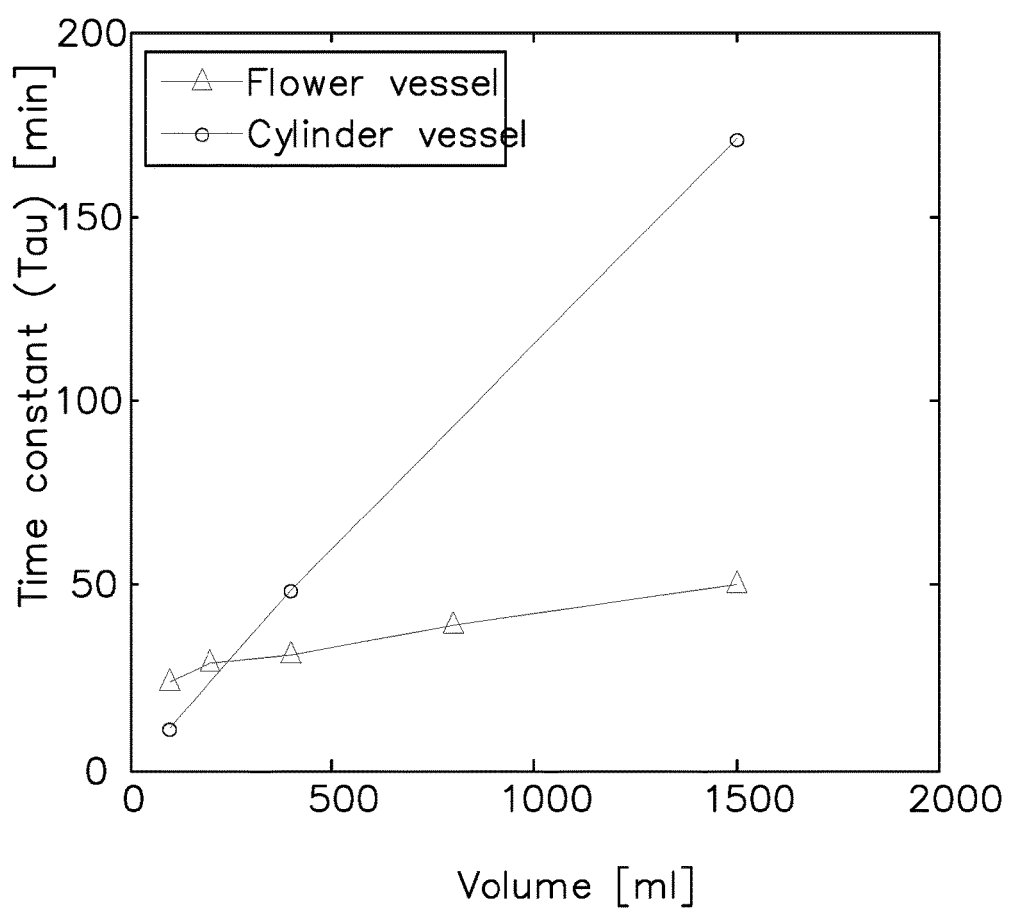
Figure 6B:
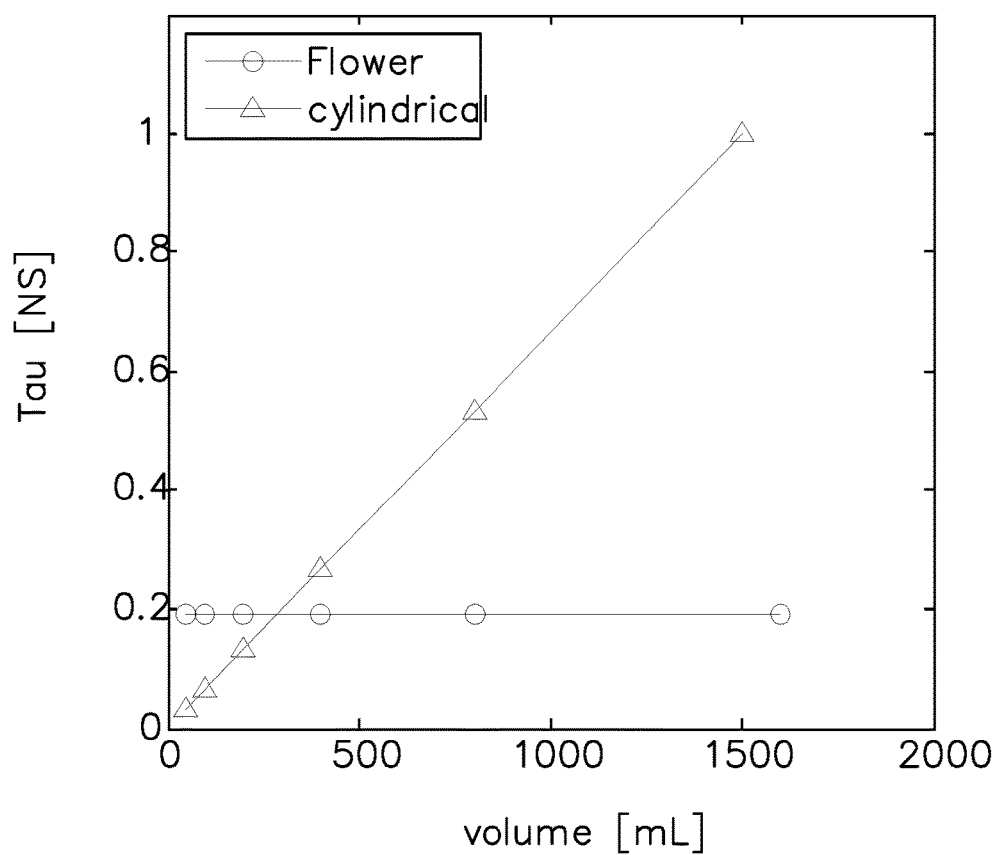

The dissolved oxygen present in the media may also be controlled through $O_2$ gas transfer from the culture media or to the culture media. As noted dissolved oxygen, the "dissolved oxygen" refers to a relative measure of the amount of oxygen that is dissolved or carried in a given medium, and the amount of dissolved oxygen may be represented in percentage. The gas transfer dynamics is measured by measuring the change in DO (dissolved oxygen) with a change in the bioreactor headspace $O_2$ percentage, at a constant agitation speed, resulting in a time constant $\tau$. The experimental data (FIG. 6A) and theoretical prediction (FIG. 6B) for time constants $\tau$ of dissolved oxygen at different volumes of culture media are almost same using a flower shaped vessel but significantly dependent on volume for a cylindrical shaped vessel, as shown in FIGS. 6A and 6B.

The experimental data, as discussed above, leads to the inference that the flower shaped culture vessel (FIG. 1 A) may comprise a design which ensures maintaining a constant or near constant specific heat transfer area and a constant or near constant specific gas transfer area simultaneously over a range of volumes in the vessel. A detailed design of one embodiment of the culture vessel is shown in FIG. 7. FIG. 7 illustrates a cross-section of the three dimensional structure of the culture vessel, with a lid 40 and which also depicts interior parts of the vessel design. As the vessel has a three dimensional structure, the vessel comprises three major dimensions of length, width, and height. A major axis of the vessel may be defined as a height, and the minor axes of the vessel may be defined as a length and width. For example, a vessel which has a circular perimeter, the minor axes of the vessel are in the same plane as the diameter of the circle (perimeter). In one or more embodiments, the culture vessel (FIG. 1 A, FIG. 7) has a perimeter, wherein a diameter (width) of the perimeter is in a range between 1 to 100 cm, or in a range between 20 to 400 mm. The depth of the vessel, such as a distance between the bottom surface and the top surface, is referred to herein as a height. In these embodiments, the vessel has a height in a range between 1 to 100 cm, or in a range between 20 to 400 mm. In one embodiment, the length by width aspect ratio is in a range between 0.3 and 3. In one embodiment of the vessel design, the length by width aspect ratio is 1. The culture vessel of the bioreactor may have a perimeter that is triangular, rectangular, square planar, pentagonal, hexagonal, polygonal, circular, elliptical or irregular in shape.

The features overlaid on the sidewall perimeter geometry that enables the vessel design to simultaneously maintain a constant sHTA given a design that maintains a constant sGTA, may be periodic wave functions that are sinusoidal, including a pure sine wave, or a Fourier series expansion. Furthermore, the wave functions maybe sinusoidal, triangular, square, rectangular, spiked, trapezoidal, pulse, or sawtooth. Further, the function applied to the perimeter may also be non-periodic. Any feature or function applied to the sidewall perimeter geometry to modify the sHTA without changing the sGTA may be applied such that the area defined by the modified perimeter geometry at a given height, h, remains unchanged from the original value designed for the given sGTA, in that the area defined by the original perimeter must not be increased or decreased with the application of the function. For a space-domain periodic function applied to the perimeter, the summation of the area for a period should be zero. For a non-periodic function applied to the perimeter, the summation of the area integrated over the length of the perimeter should be zero.

The selection of appropriate controllers is one of the requirements for maintaining the internal environment of the bioreactor for optimal cell growth. Instead of designing a complex control algorithm to deal with the varying dynamics of the multi-scalable bioreactor, in some embodiments, the multi-scalable reactor is designed such that the bioreactor dynamics is invariant to volume change. For controlling various parameters of the bioreactor, the bioreactor may comprise one or more controllers which aid in maintaining constant dynamics in the bioreactor. In one or more embodiments, the bioreactor comprises one or more controllers for controlling a gas mixing ratio, gas flow rate, heating inside the bioreactor, agitating the culture media or combinations thereof. In one example, the controller may employ a PID control law to control one or more parameters.

Figure 8A:
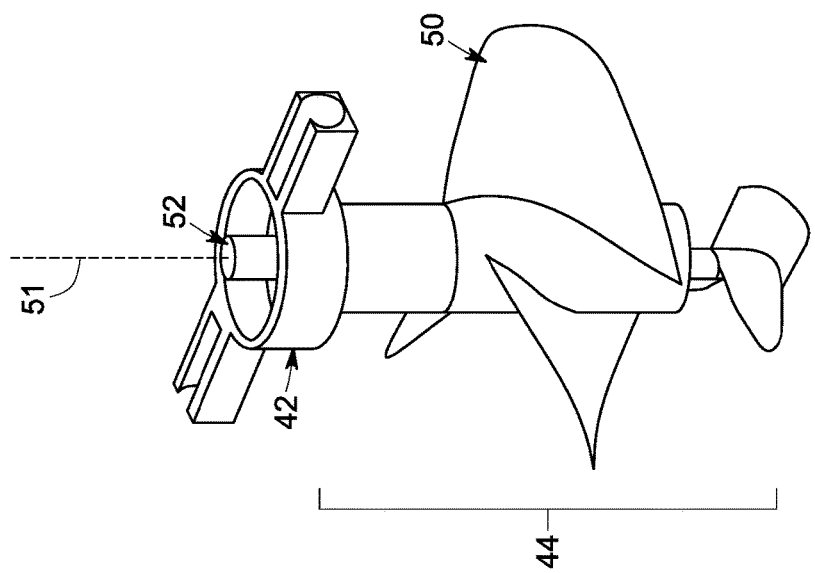

The culture vessel may require agitation for mixing the culture media, nutrients, dissolved oxygen or other gases required for cell culture. In some embodiments, the culture vessel further comprises one or more impellers for agitating the culture media. In one embodiment, the impeller 44 is coupled to the lid 40 of the vessel 10, as shown in FIG. 7. One or more impellers may be couple to the lid, to the bottom of the vessel, or both. One or more impellers may be coupled to a support, wherein the impeller support may further be attached to either top lid, or to the bottom surface or to both top lid and bottom surface of the vessel. In one embodiment, as shown in FIGS. 8 A, 8B and 8C, an impeller support 52 is attached to the top lid. The impeller design may be selected such that it provides minimum shear to the cells present in the culture media. The non-limiting examples of impeller design may also comprise a single unit impeller design or more than one part designs. A marine impeller may also be employed as that impeller causes reduced shear as compared to the other types of impellers (e.g., Rushton-type impellers). The impeller 44 (FIG. 8A) may be used for mixing the media, nutrients or dissolved gases. In further detail, an impeller 44 is illustrated by FIG. 8A, which has a wing like structure 50 and an axis 51. The top portion of the axis 51 may be coupled to the top lid, as shown in FIGS. 8 B and 8 C. FIG. 8 B illustrates, in one embodiment, the side view of the position of the impeller with respect to the overall vessel. FIG. 8 C illustrates, in the same embodiment, the front view of the position of the impeller in the vessel.

In some embodiments, the one or more impellers are operably coupled to a motor by one or more of magnetic coupling, mechanical coupling, electrical coupling, electromagnetic coupling or combinations thereof. In one embodiment, the impellers are operably coupled to a motor by magnetic coupling. FIG. 9 shows one embodiment of the culture vessel with an impeller coupled to a magnetic agitator. The magnetic agitator 60 may be located on the top of the lid 40 of the culture vessel 10 as shown in FIG. 9. The magnetic agitator 60 may be coupled to the coupling magnets 61, as also shown in FIG. 9. The magnetic agitator is further coupled to an impeller for driving the impeller in the vessel during cell culture. In this embodiment, the mechanical torque is transferred through magnetic field to drive the impeller.

The bioreactor may comprise a heating assembly comprising one or more heating units. In some embodiments, the culture vessel further comprises one or more heating units for heating the culture media, vessel and other components of the vessel. The heating units may be present at the bottom of the culture vessel to uniformly heat the culture media which is in contact with the bottom wall. The heating units may also be present at the side wall of the vessel to uniformly heat the culture media which is in contact with the side wall. One or more hating units may be present on the lid and side wall of the vessel.

In one example, the heating units may have a flexible and conformable structure. In a non-limiting example, the heating unit may be a thin film heater. Other non-limiting examples of the heater may include a heated (or temperature-controlled) bladder which can conform to the container or a heater not directly in contact with the vessel body. A container may comprise a temperature-regulated fluid circulating through the containers (such as a blanket or a jacket) and helps in heating the vessel body or cell culture media. In some other embodiments, the heating unit may comprise an IR source, a heating blanket, a water jacket or combinations thereof. A water jacket 46, in one example embodiment, may be used as a heating unit, as shown in FIG. 7. The water jacket may further be used for insulation. The water jacket may surround the outer walls of the culture vessel, either partially or completely. In some other embodiments, the culture vessel may further comprise one or more heating units in addition to the water jacket.

As noted, in one embodiment, at least one of the heating units is used to heat the side-walls of the culture vessel. The portions of the culture media, which are in contact with the side wall, may be heated uniformly or near-uniformly by use of the heating units. The heating unit present at the side of the vessel, which may be referred to herein as a "side-heater". FIG. 10 further shows integration of a side-heater 62 to the culture vessel 10. In some embodiments, a portion of a heating unit (side heater) 62 configured to heat at least a portion of a vessel body 10. By way of example, initially, the heating component 62 may be configured to heat the side wall of the culture vessel and the transmitted heat further heat the culture media. The side heater 62 may be used to heat the culture media at 37° C. Various designs of the side heater 62 may be possible. The side heater 62 may be directly glued to the disposable culture vessel and the heater may also be disposable. The side heater 62 may be integrated with the non-disposable system and positioned such that the heater is capable of heating the side wall of the vessel. In one embodiment, a shell having a structure that matches with the outer surface profile of the disposable vessel may be placed between the heater and the vessel. In this embodiment, a foam layer may be placed in between the heater and the vessel to reduce the air gap. Further, the shell may be a good thermal conductor to reduce vessel surface temperature gradients and reduce thermal time constants with heating or cooling the vessel. Further, the heating units may comprise a thermal conductor, which may configure to facilitate transfer of heat from the heater 62 to the body 10 of the vessel. Further, the thermal conductor may facilitate uniform distribution of heat on the vessel body 10. In one embodiment, the heating unit may be made of one or more parts. Further, the one or more parts of the heating component 62 may be configured to be conformably disposed around a determined portion of the vessel body 10 including the bottom of the vessel. The heating assembly may further comprise a lid heater 63 to heat the lid 40 of the vessel. The lid heater 63 may be a thin layer disposed on the top of the lid 40, as shown in FIG. 10. By way of another example, the heating component 63 may also be used to heat the lid to have a single internal temperature for the culture vessel.

The temperature of the culture media may be controlled to maintain a constant temperature during the cell culture operation. In some embodiments, the bioreactor further comprises one or more temperature sensors 66, as shown in FIG. 10. In the illustrated embodiment, the temperature sensor 66 is operatively coupled to the internal vessel media temperature through the vessel wall. In yet another embodiment, a temperature sensor may be directly integrated into the vessel to provide a direct temperature measurement and the temperature sensor may be disposable. In one embodiment, the heating units may include a temperature sensor that is operatively coupled to the side heater 62, a lid heater 63, the vessel body 10 or combinations thereof. Consequently, a temperature sensor may be configured to sense a temperature of the heating units 62, 63 and/or the body 10. Non-limiting example of the temperature sensors may include thermocouples, thermistors, or resistance temperature devices (i.e., RTDs). In one embodiment, the bioreactor comprises a non-invasive temperature sensor 66 coupled to the bottom of the bioreactor vessel, as shown in FIG. 10.

Further, the heating units may further include a temperature controller (not shown) operatively coupled to the temperature sensors and operatively couple to temperature sensors coupled to the heating units to control a temperature of the heating units and/or the vessel body. The temperature sensors may provide a temperature feedback to the controller to the culture media to control the temperature. In some embodiments, the temperature sensor may be coupled to a temperature controller to provide a temperature feedback control mechanism. In one or more embodiments, the bioreactor further comprises one or more temperature controllers for maintaining the temperature of the culture media. The bioreactor further comprises one or more temperature controllers to control a temperature of the bioreactor lid 40.

Inside the bioreactor vessel, the temperature is controlled at a desired temperature, for example, at 37° C. The constant heating to the vessel wall, culture media and other components of the culture vessel are heated up. The heating of media results in evaporation of water from the culture media. The evaporation of water from the culture media may cause a change in media volume. For example, due to evaporation of water from the liquid media, the effective volume of the media is reduced. If the volume of the water vapor lost from the vessel is high, the culture media volume may decrease significantly. The decrease of water from the culture media may have a negative effect onto the cells due to increased osmolality of the medium. For example, when the cell culture media volume is 50 mL, water loss of 2-5 ml may cause significant change in medium osmolality which may affect the cell growth. The generated water vapor may reduce the volume of the cell culture media due to two different mechanisms. The first mechanism is evaporation of water from the surface of the culture media, which may further condense on the inner surface of the vessel lid 40. The second mechanism of water loss may be through the egressing gas through the gas outlet port 76 from the culture vessel, as shown in FIG. 10.

In some embodiments, to avoid evaporation or reduction of liquid from the culture media, a lid may be used for the bioreactor vessel. In some embodiments, the bioreactor further comprises a bioreactor lid 40, as shown in FIGS. 7, 9 and 10. If the temperature of the lid is less than the temperature of the culture media or evaporated liquid from the media, then the evaporated liquid condensates in contact with the lid 40 and may form water droplets at the inner surface of the lid 40. For example, the lid inner surface temperature is lower than 37° C., when the vessel has an inner temperature of 37° C. In this condition, the water vapor inside the bioreactor may be condensed on the inner surface of the lid and form drops of water hanging from the inner surface, which are effectively removed from the culture medium. The total volume of water droplets hanging from the lid inner surface may be significant (e.g., up to 20% of the initial culture media volume).

To avoid evaporation of the liquid media, the temperature of the lid may be maintained such that the evaporated liquid from the media does not condense on the lid inner surface. An anti-condensing heater on the lid may be designed to eliminate water condensation on the inner surface of the bioreactor lid. By increasing the temperature of the lid to higher than 37° C. (e.g., 37.5° C.), the condensation problem may be avoided. The culture vessel 10 further comprises a lid heater 63 at the lid 40, as shown in FIG. 10.

As noted, a second mechanism of water loss may be through the egressing gas from the gas outlet port. During the cell culture process, one or more gases may be supplied into the bioreactor vessel using the gas inlet port. Gas may exit the bioreactor vessel from the gas outlet port. The supplied gas to the culture vessel may be dry (without water vapor). When the gas exits from the vessel, the outgoing gas may carry water vapor generated from the media. Significant water loss from the culture media may affect the cell growth. To address this issue, (FIG. 11) an off-gas condenser 84 may be employed, wherein the off-gas condenser is wrapped around the off-gas tube or gas outlet tubing 76 and is used to condense the moisture in the effluent gas from the vessel. This condenser is interchangeably referred to herein as a "off-gas condenser" or "outlet condenser". The off-gas condenser, in some embodiments, may be physically implemented around or adjacent to the gas outlet tubing, for example, by using a water-cooled loop or a thermo-electric Peltier cooler. Due to gravitational force, the droplets of water may be collected to the bioreactor vessel. The off-gas condenser may be maintained at a low temperature (e.g., 5° C.). When the gas passes through the gas outlet, due to lower temperature of the outlet tubing, the water vapor may condense on the chilled sidewall of the outlet tubing and return to the bioreactor vessel due to gravity. In this way, water loss from egressing gas may be reduced to zero or a negligible amount. In some examples, without using an off-gas condenser and at 100 ml/min of gas flow rate, the water loss may be about 5 ml/day. In one exemplary embodiment, using a flow rate of 100 ml/min, the water loss using the off-gas condenser was about 1.3 ml/day. Under same conditions of flow rate of 100 ml/min and using an off-gas condenser, the water loss associated with the outlet gas flow may be reduced to less than 1 mL per day.

In some embodiments, the culture vessel may further comprise one or more sensors, such as bottom dot sensor 70 to measure pH and DO, as shown in FIG. 10. The pH and DO of the media may be adjusted by changing the relative percentages of the influent mixed gas flow. Further, by using a pH sensor, the pH condition of the media may be determined and a defined amount of acid or base may be added depending on the requirement. In one example, an acid or a base is added through one or more conduits to the culture medium for adjusting pH of the medium. If the medium is required to be more acidic, an acid may be added and the sensor helps detecting the actual pH of the culture media. If the medium is required to be more basic, the sensor provides a signal, and a base may be added to achieve a desired pH.

The bioreactor may further comprise one or more conduits, wherein the conduits are used for adding or removing culture media, nutrients, cells, gases, acid, base or combinations thereof to the vessel. The conduits used for adding or removing cells, culture media, nutrients or gases may be sterilized before coupling to the bioreactor. The conduits used for adding cells, culture media, nutrients or oxygen may also be pre-connected with the bioreactor and may be sterilized prior to use. Further, connections to the conduits may be made using standard aseptic techniques (standard luer, luer-activated swabbable port, spike and membrane, etc.) typically performed in a biosafety cabinet. Connections of the conduits with the other conduits may be made using tube fusing devices to maintain sterility.

The conduits may also be used for adding cells to the vessel. In some embodiments, the media and media carrying cryopreserved cells may be added to the vessel as a cell-suspension using a conduit. Connections of the conduits to the culture media, nutrients, gases may also be made in a non-sterile environment if the conduit attached to the bioreactor has a sterilizing in-line filter (e.g., 0.4 m filter).

The bioreactor may comprise multiple ports, which may include inlet ports and outlet ports and the ports may be located on the lid, vessel side walls, or bottom surface of the vessel. The ports are coupled to the conduits for fluid, nutrient or gas entering or exiting from the bioreactor vessel. The conduits which are used for adding culture media or nutrients may be referred to herein as "feeding lines" (not shown). The feeding lines are connected to "feeding port" 74 of the bioreactor, as shown in FIG. 10. As noted, the bioreactor is configured to accommodate an expandable medium volume, wherein the additional media may be added to the culture vessel by one or more feeding lines via feeding ports 74.

The bioreactor may further comprise one or more conduits for supplying gas inflow, which may be connected to a gas inlet port 78 (FIG. 11). The bioreactor may further comprise one or more conduits for egressing gas outflow, which may be connected to gas outlet port 76, as shown in FIGS. 10 and 11. As noted, the outlet port 76 on the lid 40 may be used for gas outlet from the culture vessel, as shown in FIG. 9. In some embodiments, the gas inlet port 78 and/or gas outlet port 76 (FIG. 11) comprise one or more filters. With a sufficiently small pore size, the filter units help in maintaining sterility and avoid entry of unwanted particles or unintended microorganisms. In some embodiments, wherein the gas outlet port is directly connected to a gas outlet tube and at the end of the gas outlet tubing, the tubing may contain a filter, such as a filter of 0.22 micron to create a barrier to separate the sterile environment in the bioreactor vessel and the non-sterile environment outside of the vessel.

As illustrated in FIG. 11, the gas inlet port 78 may comprise a heater 82 to heat the incoming gas or gases and the gas outlet port 76 may comprise an off-gas condenser 84 to condense outgoing vapor generated from the culture media. Due to condensation of the vapor using the condenser, the liquid remains in the culture vessel and prevent water loss. In presence of ambient temperatures, a filter on the outlet gas conduit may condense a portion of the water vapor exiting the bioreactor. Further, water droplets may accumulate at the filter unit, which may result in blocking the filter. To help address this issue, the off-gas condenser 84 may be placed between the vessel and the 0.2 micron filter 77 on the gas outlet tubing connected to the outlet port 76 (FIG. 11), which forms water droplets to remove the water vapor before the egressing gas reaches to the filter unit. By removing the water content in the egressing gas flow, the off-gas condenser 84 also helps to prevent blocking of the filter unit.

In one or more embodiments, the vessel further comprises conduits for withdrawing the culture media from the vessel for sampling and/or transferring the cell culture media with cells to a downstream container, vessel, or device under sterile condition. The conduits which are used for transferring cells from the vessel for analysis, sub-culturing, or may be referred to herein as "sampling line" connected to the "sampling port", the liquid sampled is considered herein as a "sample". Sampling port is generally used to take a small amount of cell culture out of vessel. Sampled culture may or may not be sterile, wherein the sample culture is usually used for off-line measurements. The sampling port 72 may be located on the side wall of the vessel, as shown in FIG. 10. In another embodiment, the sampling port may be located at the top of the vessel with a conduit internal to the vessel connected to the internal portion of the port that extends below the liquid level in the vessel. The conduits may be made of polymer, glass or steel. The conduits may comprise one or more valves to control the flow of culture media, gas, cell-suspension, nutrients, acid or base. In yet another embodiment, the sampling port may be located on the bottom surface of the vessel.

In some embodiments, the bioreactor system further comprises a two-door cover 80 on the top of the vessel lid 40, as shown in FIG. 11 and the dissection view of the two-door cover 80 is shown in FIG. 12. In one or more embodiments, the two-door cover comprises an inlet gas heater 82. In some embodiments, the two-door cover comprises an off-gas condenser 84. In other embodiment, the two-door cover comprises of both an inlet gas heater and an off-gas condenser. The evaporated liquid vapor, which may evaporate out from the outlet 76, converts to liquid again by condensation as the outlet comprises an off-gas condenser 84. The door may further comprise a heating surface 86, which is the inner surface of the door and is in contact with the top surface of the lid when the vessel is covered with the lid and the doors for the purposes of heating the lid surface and preventing condensation on the lid surface internal to the vessel volume, as shown in FIG. 12.

In one or more embodiments, the culture vessel may comprise a bag or a flexible container to dispose inside the culture vessel, wherein the cells are grown inside the flexible container or the bag. In these embodiments, the cryopreserved cells may be added to the culture bag or flexible container followed by adding the culture media for cell culture. In some other embodiments, the bag is pre-filled with the cell-inoculum and then may be placed in a culture vessel followed by addition of culture media to the bag for cell growth. The bag may be a disposable culture bag, such as culture bags from Wave™ or Xcellerex®. The use of bag or flexible container helps maintaining the sterility of the culture vessel. Moreover, the autoclaving or sterilizing the big culture vessel may be avoided by using the cell culture bags or flexible container.

In one or more embodiments, the bioreactor vessel, the culture bag or flexible disposable container for culturing cells further comprises a biocompatible coating, such as a biomolecular coating. One embodiment of the bioreactor vessel comprises a biocompatible coating on an inner wall of the culture vessel. The bimolecular coating may be selected depending on the requirement of different cell lines. In one or more embodiments, the culture vessel comprises biomolecular coatings that comprised of biologically derived proteins or peptides, recombinant proteins or synthetic peptides or growth factors that activate, promote proliferation or differentiation of specific cell populations. The proteins may include, but are not limited to, notch ligands, anti-CD3 antibody and anti-CD28 antibody. The material selection for the vessel may be based on the material's characteristics to withstand adequate amount of heating and continuous agitation during cell culture. In some embodiments, the culture vessel is made of glass, polymer, ceramic, metal or combination thereof. In one embodiment, the culture vessel of the bioreactor is made of thermoplastic. In some other embodiments, different parts of the vessel may be made of different materials, for example, a temperature sensor port may be made of glass or stainless steel. The gas outlet tube may be made of metal or polymer. The impeller assembly located in the vessel may comprise permanent magnetic materials. In some embodiments, the vessel further comprises multiple tubings or filter units, which are made of polymeric material.

In some embodiments, the culture vessel is made of a plastic material and the vessel is disposable. The disposable parts of the bioreactor may comprise the plastic vessel with lid (FIG. 7), the conduits such as feeding port, sampling port, port for passing gas, filters located in different passages such as the ports to carry gases or vapor, or the conduits for inoculum transfer.

In some other embodiment, the culture vessel may be non-disposable. The non-disposable culture vessel may be made of for example but not limited to, glass, polymer or metal. The non-disposable vessel may be autoclaveble or may be sterilized by gamma sterilization or gas sterilization (e.g., using hydrogen peroxide or ethylene oxide). The lid and other components of this vessel may also be reusable.

In one or more embodiments, the bioreactor is a reactor is agitated with a one dimensional shaking, a reactor agitated with two dimensional shaking, a reactor agitated with three dimensional shaking or combinations thereof. In some embodiments, the bioreactor is a stirred tank bioreactor, a reactor with a rocking or rolling motion, a perfusion bioreactor or combinations thereof.

In one or more embodiments, a kit comprises a disposable bag; one or more disposable tubings; and a bioreactor comprising: a culture vessel as described above. In some embodiments, the bag comprises media for culturing cells.

In one or more embodiments, the culture vessel may be integrated to a bioreactor system. The bioreactor system may be manually operated or may be operated automatically. FIG. 13 illustrates one exemplary embodiment of a process of integration of a bioreactor system, wherein a culture vessel 10 and a sample loading vial 90 are coupled together in a process step 1 (FIG. 13), a blade 92 for sterile tube fusion is inserted into the system 94 in step 2. In step 3, the culture vessel and sample loading vial are further coupled to the system 94 to form the overall integrated system 96, as shown in step 4 of FIG. 13. The bioreactor vessel of the system 96 may further be couple to a media bag 100 (FIG. 13). The integrated system may be automated, wherein a switch (not shown) may be used to control the bioreactor system.

Further, the culture vessel may comprise an outlet passage, which is coupled to a sampling assembly or conduit, which may further be operatively coupled to an external device, such as an analytical device, a cell harvester, a bioreactor of larger size, a chromatography system or any analytical system. In some embodiments, the culture vessel may comprise an outlet passage, as referred to herein as sampling port 72 (FIG. 10) coupled to a sampling assembly or conduit, which may further be operatively coupled to an external device, such as an analytical device for off-line measurement of cell growth.

In a non-limiting example, the external device is a cell harvester or a cell-concentrator, a bioreactor or a filtration device. In some embodiments, wherein the external device is a cell-harvester, the external device is configured to receive the cultured cells mixed with the growth media after expanding the cells in a bioreactor system in large scale. In these embodiments, the culture vessel may comprise an outlet passage, as referred to herein as harvesting port (not shown) coupled to a cell harvester. Harvesting port may be used to transfer a large amount or all of the cell culture of the vessel to a cell harvester. The cultured cells are transferred to a harvester under sterile condition followed by harvesting the cells from the media to achieve concentrated cells for downstream applications, such as different cell therapeutic applications. For example, the concentrated cells, such as immune cells (e.g., T-cells) may be injected to a patient for different immunotherapeutic applications.

In some embodiments, the external device is another bioreactor to continue the process of cell culture, wherein one or more specific protein production is a major objective. Proteins, such as recombinant proteins, antibodies are produced in the bioreactor followed by purifying the proteins from the cells, media or other impurities. The proteins produced in the external device, such as in a bioreactor, may further be used for biopharmaceutical applications.

In some other embodiments, the external device may further include a filtering device or a chromatographic device. The filtering device or chromatographic device may be used for filtering the cells, or any biomolecules such as proteins or nucleic acids for further downstream applications. In some embodiments, the produced proteins or nucleic acids are subjected to chromatographic separations before use in cell therapy, biopharmaceuticals, clinical or research applications.

In some embodiments, the bioreactor system may further comprise a sparging port, which may be placed under liquid (media) level. The sparging port is used to flow gas to the culture. The gas inflow through the gas inlet present on the lid may be delivered to the headspace, while the gas through the sparging port may be delivered into liquid directly, forming bubbles of various sizes, depending on sparging port design. Sparging port is developed to provide a higher gas transfer rate to the culture, usually for supporting high density cell culture or a culture requires high volume of oxygen.

In some embodiments, as illustrated in FIG. 13, the bioreactor comprises a controller unit 110 may be used to collectively represent various control devices employed in the automated bioreactor system 96, where the control devices are configured to control and regulate operation of the automated system 96. By way of example, in the illustrated embodiment, the controller unit 110 may be configured to control an input flow of the culture medium using a flow rate controller. Further, the flow rate controller may also be configured to control outflow of cultured cells through the sampling path 72. Advantageously, the flow rate controller may facilitate enhanced mixing of cells, culture medium, nutrients, oxygen or other gases by controlling the inflow and outflow rates of culture media, nutrients or gases. In some embodiments, the controller unit 110 may employ sensors to sense parameters being controlled. The bioreactor system may further comprise one or more controllers (not shown) for controlling the media temperature using one or more heating units. As noted, the controllers may present to control the temperature of the lid heater, or control the power to the anti-condensing cooler on the outflow gas.

In the bioreactor system, the disposable components may be vertically loaded into the system, as shown in FIG. 13, steps 1-3. In some embodiments, the bioreactor system comprises door(s)/cover(s) 80 (FIGS. 11 and 12) on the top surface of the vessel lid. When the door(s)/cover(s) are open, the disposable may be integrated with the device. Then the door(s)/cover(s) will be closed for system operation. When the disposable is placed into the device 94, sensors may be aligned automatically to the disposable so that no user actions are required for sensor alignment. After the disposable is vertically loaded inside the bioreactor system 94, the feeding ports 74 are placed at the proximity of the peristaltic pump, forms a complete system 96.

Step 4 of FIG. 13 illustrates an example of automated system 96 comprising a controller unit 110 and a processor unit 120. The system may further comprise a pump (not shown). In a non-limiting example, the pump may be a peristaltic pump. The pump may be configured to facilitate transfer of the culture media from a culture media source and disposed in the culture vessel 10 through the conduits. The culture medium source 100 may be operatively coupled to the culture vessel 10 using an inlet passage (not shown). Further, the pump may be configured to facilitate transfer of the culture media from the culture bag 100 to the culture vessel 10 incrementally, depending on the requirement, at a pre-determined rate. The pump may also be used to pump the cells contained in the vial 90 using the media contained in bag 100 and transfer to the vessel 10.

Further, the integrated system 96 comprises a processor unit 120, which may be configured to process data from the controller unit 110. In certain embodiments, the processing unit 120 may also be coupled to one or more user input-output devices (not shown) for receiving commands and inputs from a user. The input-output devices, for example, may include devices such as a keyboard, a touchscreen, a microphone, a mouse, a control panel, a display device, a foot switch, a hand switch, and/or a button. Moreover, the processor unit 120 and/or the controller unit 110 may be configured to be coupled to other devices, such as, but not limited to, a bioreactor, a cell harvester, the culture media source, the pump or combinations thereof, to control or monitor the operation of these devices. Further, the processor unit 120 and/or controller unit 110 may be configured to be coupled to an automated sampling device that is operatively coupled to the sampling line and used to monitor specific parameters of the cell culture, including but not limited to cell count, cell viability, glucose, lactate, DO, pH, osmolality, $pO_2$, and $pCO_2$.

In an alternative embodiment, each controller of the controller unit may have respective individual processors. In some embodiments, the processor unit 120 and/or the controller unit 110 may be configured to store the related data in a storage repository (not shown). In one embodiment, the storage repository may include devices such as a hard disk drive, a compact disk-read/write (CD-R/W) drive, a Digital Versatile Disc (DVD) drive, a flash drive, and/or a solid-state storage device.

Further, the automated system 96 may include an output device that may be configured to display data representative of the progress of the cell culture or growth in the automated seed train, or any other parameters pertinent to the operation of the automated system. In one example, the output device may be configured to display the sensed data sensed by one or more sensors employed in the automated system 96.

Advantageously, the automated system 96 may include provisions for simply adding the cryopreserved cells followed by adding culture media and turning on a power supply for the system 96, e.g., by using a switch, to initiate an automated seed train process. Accordingly, the automated system 96 performs the seed train process with minimal operator intervention, thereby reducing the possibility for human intervention, contaminations, human errors and unpredictable results associated therewith.

The culture vessel may also be sterilized before use, may be by using autoclave, gamma sterilization, UV sterilization and the like. The lid, impeller and one or more other parts located inside the culture vessel may also be sterilized before use. Further, in one embodiment, sealed conduits or conduits embodied with filter unit may also be combined with the vessel to make a bioreactor system that may be a single pre-sterilized disposable unit, thereby making the automated system 96 even less prone to contamination by preventing introduction of contaminants from a previous batch, or the like. The culture media used for cell culture is sterilized media, either prepared in-house or purchased from outside.

Moreover, the automated system 96 may be operated by a non-trained operator. Since the automated system 96 is capable of providing sterile access of adding culture media followed by cell culture in a sterile bioreactor environment, a laminar hood may not be required, which may significantly reduce floor space requirement and infrastructural cost.

In some embodiments, the automated system 96 may be configured to effectively operate in an automated manner. Advantageously, the system is configured to enable sterile access and transfer of cryo-preserved cells and culture media to the bioreactor vessel for further cell culture processing. In a particular example, the culture vessel 10 may be used for culturing the cells to several billion cells by inoculating the cells and scaling up the culture process by adding additional media volume in a single bioreactor vessel.

In certain embodiments, the automated system 96 comprising the auto seed train culture vessel 10 may provide an automated production facility for biopharmaceutical or bioprocess industry with the ability to start with frozen or cryo-preserved cells and produce an expanded cell culture using the bioreactor system. The same vessel may be used for different culture volume, depending on the customer requirement.

Embodiments of a method for culturing cells are provided, wherein the method comprises providing a bioreactor comprising a culture vessel, seeding the cells to the culture vessel, adding a first volume of cell-culture media to the culture vessel, culturing the cells in the culture vessel to achieve a desired cell-density, and adding a second volume of cell-culture media for increasing the volume of the cell-culture media at a predetermined level to achieve a desired cell density. In this embodiment, the bioreactor dynamics remain minimally affected by maintaining the specific heat transfer area and the specific gas transfer area at different volumes of culture media.

In some embodiments of the method, the second volume of cell-culture media is added incrementally to increase the volume at a predetermined level. The term "incrementally" may include a continuous feeding or addition of media to the vessel, a non-continuous addition of media to the vessel or both. As noted, in some embodiments of the method, the culture vessel has a capacity to accommodate the cell-culture media volume between 20 ml to 5 liter without introducing a significant change in bioreactor dynamics by maintaining the specific heat transfer area and the specific gas transfer area at different volumes. In these embodiments of the method, the cells are seeded to the culture vessel from a cryopreserved cell-stock.

In some embodiments, the method steps beginning with and including the steps of thawing the cryo-preserved cells, transferring the cells to the culture vessel, followed by the step of adding a first volume of culture media for culturing cells. The second volume of the culture media may further be added to the culture vessel as a next step for culturing cells in a large scale. The method steps as described herein may be automated. In some embodiments, the first volume may be the volume that transfers the cells from the cryo-vial to the bioreactor vessel. In this embodiment, the seed volume is larger than the volume in the cryo vial, and to reach the seed volume, a second volume of media may be added to the vessel for culturing cells.

In some embodiments, the method further comprises controlling a gas flowrate within the culture vessel. In some other embodiments, the method further comprises controlling one or more environmental conditions of the culture-media of the bioreactor. The one or more environmental conditions for cell-culture comprise temperature, pH, dissolved oxygen, agitation or combinations thereof. The method may further comprise controlling a composition of cell-culture media. A constant temperature may be maintained during the seeding and culturing cells. In some embodiments of the method, a constant pH and dissolved oxygen may also be maintained during seeding and culturing cells. As noted, speed of the impellers may also be controlled to agitate the cells in the culture media.

The bioreactor may be configured to seed and culture cells selected from bacterial cells, animal cells, plant cells, fungi, insect cells, microbes, virus cells, stem cells or combinations thereof. The cells may be selected from bacterial cells, mammalian cells, stem cells or combinations thereof. The cells may comprise adipose derived stem cells, mesenchymal stem cells, induced pluripotent stem cells, embryonic stem cells or combinations thereof.

In a particular example, the sample may be a cryo-preserved sample. In one example, the cryo-preserved sample may be thawed to form a liquid cell suspension to enable transfer of the seed inoculum. In some embodiments, the cryo-preserved cells may be heated rapidly to form a liquid cell-suspension. It may be noted that a culture media is usually stored at about 4° C. However, using the cell culture media having a temperature of about 4° C. or below may negatively impact on cell growth. Consequently, it may be desirable to pre-warm the growth medium at least to a room temperature and use for cell culture.

FIG. 14 is an exemplary method 130 for culturing cells using an automated seed train bioreactor comprising a flower shaped culture vessel 10, wherein an incremental addition of culture media does not affect key parameters affecting the bioreactor dynamics, such as specific heat transfer area or specific gas transfer area. The culture media may be added to the culture vessel for multiple times without changing the bioreactor dynamics of the vessel. The method may be partially automated or completely automated depending on the requirement. Another advantage of using the bioreactor vessel is that the culture media may be added to the culture vessel for multiple times without using the multiple vessels.

The first step 132 of the method comprises providing a cell culture vessel, such as a container or vessel as a part of seed train process for cell growth or inoculation. The culture vessel is configured such that an incremental addition of culture media does not affect the bioreactor dynamics. The culture vessel is designed such that a heat transfer area or gas transfer area remain constant. In one or more embodiments, the culture vessel may comprise a bag or a flexible container to dispose inside the invariant-designed shaped culture vessel, which is referred to herein as a "flower shape vessel".

In the next step 134, a small inoculum of cells, such as an aliquot of cryo-preserved cells is added to the cell culture vessel. The inoculum of cells may be a cryo-preserved or frozen sample of cells. In one example, the cells may be mammalian cells. In some embodiments, the frozen cells are thawed before adding to the culture vessel. In some other embodiments, the frozen cells are rapidly heated to form a cell suspension for further culturing the cells. In these embodiments, a heating component may be coupled to the container that contains cryo-preserved cells. The heating component may be configured to thaw and heat the cryo-preserved sample, which may initially be at −80° C. or below to a temperature of about 37° C. Alternatively, a water bath or bead bath may be used to heat the cryo-preserved cells. In one embodiment the cells may be added to the vessel through a conduit connected to the container of cryo-preserved cells. In another embodiment, the cells may be added directly to the vessel through a port present on the vessel, specifically under sterile conditions within a laminar flow hood.

At block 136, the first volume of cell culture media is added to the culture vessel. The culture vessel may be operatively coupled to one or more external devices, such as, but not limited to a growth medium source, a pump, a bioreactor, or combinations thereof. The cell culture media may be stored in an external device, such as a container located outside of the bioreactor. The culture media may be transferred from the container that stores cell culture media to the culture vessel for initiating the cell culture process. Further, the cell culture media may be used to transfer and flush the thawed cryopreserved cells from the cryo-preservation container and/or a coupled container. Additionally, the container that stores cell culture media may also be coupled to a heating component, where the heating component may be configured to pre-heat the culture media prior to introducing in the culture vessel.

Further, at block 138, the cell suspension is mixed thoroughly with the added culture media in the vessel. The mixing of the culture media with the cell suspension may initially be achieved by rapidly flowing the cell culture media into the vessel containing the seed cells to promote mixing. Additionally, the mixing of the culture media with the cell suspension may be achieved by using an impeller inside the vessel or using a stir bar. The speed of the impeller or stir bar may be such that it ensures mixing of the culture media with the cells, avoiding any excessive shear force on the cells which may damage the cells. The mixing of the cells and culture media may be under intermittent or continuous agitation. Additionally, the mixing may be achieved by shaking of the culture vessel. The shaking may be achieved by using one dimensional or two dimensional shaking, such as using an orbital motion, a wave motion, or a rolling and rocking motion of the vessel.

Further, at block 138, the culturing of the cells is continued in the culture vessel. In particular, the cells are expanded to a higher numbers. The cell growth is executed in a desired temperature of, for example 37° C. The temperature of the cell culture media may be maintained using the heating unit, temperature sensors and temperature controller. The temperature sensors (e.g., thermal couples) may be used to sense the temperature of the culture media, directly or indirectly, and the heater respectively. Moreover, a temperature controller may be used to modulate the temperature of the culture media and the inside environment of the vessel to about 37° C. Maintaining the temperature at or below 37° C. ensures that the cells are not damaged due to overheating. The temperature of the culture media may vary with the cell types. The cell culture may also be influenced by the presence or absence of media nutrients or gases, such as oxygen and carbon dioxide. The cell culture may also be affected by pH of the media. Consequently, the culture media introduced into the vessel may be at a desired temperature, pH, and contain media nutrients or dissolved gases (oxygen, carbon dioxide) suitable for cell growth. For large scale cell culturing, cells and culture media are also under constant or intermittent agitation, which results in proper mixing of media nutrients or gases and enhance cell culture.

The next step 142 of the method is to add a second volume of culture media to the culture vessel for culturing cells in a larger scale. The vessel is configured such that the vessel can accommodate a second volume or a third volume or a fourth volume of the culture media for culturing cells, wherein the added volume of culture media does not affect or does not significantly affect the dynamics of the bioreactor. The second volume of culture media is added to the culture vessel using sterile conduits and the transfer process maintain a sterility of the cell culture environment. In some embodiments, the conduit for adding additional media may be the same as the conduit used to add the seed cells and cell culture media. In some embodiments, the flow rate of the culture media and the volume of culture media required to provide a large scale cell culture facility may be calculated based on one or more of: 1) desirable cell recovery and 2) desirable cell density in the expanded cells.

The next step 144 refers to a large scale cell culture for expanding cells to get a higher number of cells. Like the second volume added to the vessel in previous step 142, the third volume, fourth volume, fifth volume and so on may be added incrementally to the vessel for culturing cells in large scale. The incremental addition of media to the vessel does not affect the sterility or dynamics of the cell culture in bioreactor. Large scale cell culture is advantageous for biopharma, bioprocess or biotherapeutic industry. For culturing cells, the desired conditions of temperature, pH or dissolved oxygen may be maintained in step 144.

Further, at next step 146, after the completion of cell culture, the cells with culture media may be transferred to an external device, for example, a subsequent bioreactor or a cell-harvester device for harvesting cells. The expanded cells may be efficiently recovered from the culture vessel and transferred from the culture vessel to the external device. In a particular example, after culturing the cells, a peristaltic pump may be turned on to drive out the cells and the culture media through a sampling path of the bioreactor.

In some embodiments, a seed train workflow involving the bioreactor vessel may also be used as a continuous source of cells for the duration of a production campaign, such as rolling seed train. Based on the manufacturing schedule, part of the cells from the bioreactor vessel may be used to inoculate the first stage of the inoculum seed train, which typically comprises 20 L media volume. The cell culture from the first stage added to the subsequent two stages, such as second stage (100 L) and third stage (750 L) of the inoculum train followed by the production vessel (2000 L) run. Fresh medium may be added to remainder part of the culture within the bioreactor vessel and expanded the cells till the desired cell density is achieved. This ensures uninterrupted availability of cells for a second inoculum seed train and also a backup cell supply that may re-establish manufacturing operations in case of a run failure.

There may be no operator intervention required for the steps 134 to 146, when the bioreactor system is completely automated. Alternatively, a minimal operator intervention that may be required for providing culture vessel and for adding cryo-preserved cells to the vessel. In some examples, the bioreactor requires a separate independent switch to be switched on to power the pump and the other components involved in the transfer of the culture media to the vessel, to run the impellers, to add the gas mixture or nutrients or to further transfer the expanded cells to an external device.

Further, the automated system may be placed either on a bench or a cart, thereby increasing the flexibility of the entire cell production floor. Further, the automated system may not require a skilled person to operate the system. Further, disposable nature of the culture vessel or conduits allows for rapid change over in the production facility. Moreover, the culture vessels, bioreactor systems and methods of the present specification are automated to a great extent after installation of the culture vessel and the vials containing cryo-preserved cells and are thus less labor intensive.

One or more different types of cells may be cultured using the multi-scale seed train bioreactor. The cells may include, but are not limited to, adherent cells, non-adherent cells, suspension cells, suspension-adapted adherent cells, immune cells, stem cells, plant cells, animal cells, bacterial cells, fungal cells, insect cell-line or combinations thereof. In one embodiment, the cells are adherent cells, which may include embryonic stem cells, mesenchymal stem cells or induced pluripotent stem cells.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for culturing cells, comprising:
   (a) providing a bioreactor comprising a culture vessel, for seeding and culturing cells by adding cells and a cell-culture medium to the bioreactor, wherein the culture vessel comprises at least a side wall and a bottom surface, wherein the culture vessel is configured such that a specific heat transfer area (sHTA) and a specific gas transfer area (sGTA) of the culture vessel are constant with respect to a change in a volume of the cell-culture medium in the culture vessel, wherein the specific heat transfer area at a medium height 'h' is defined by equation (1) and the specific gas transfer area at a medium height 'h' is defined by equation (2), and wherein V is the total volume of the cell-culture medium:

$$sHTA(h) = HTA(h)/V(h) \qquad \text{equation (1), and}$$

$$sGTA(h) = GTA(h)/V(h) \qquad \text{equation (2);}$$

(b) seeding the cells in the culture vessel;
   (c) adding a first volume of cell-culture medium to the culture vessel;
   (d) culturing the cells in the culture vessel to achieve a desired cell-density; and
   (e) adding a second volume of the cell-culture medium to increase the volume of the cell-culture medium to a predetermined level to obtain a desired cell density.

2. The method of claim 1, further comprising controlling one or more environmental conditions of the cell-culture medium of the bioreactor.

3. The method of claim 2, wherein the one or more environmental conditions for the cell-culture comprise temperature, pH, dissolved oxygen, agitation, gas mixing ratio, gas flow rate, or combinations thereof.

4. The method of claim 1, further comprising controlling a composition of the cell-culture medium.

5. The method of claim 1, wherein the second volume of the cell-culture medium is added incrementally to increase the volume to the predetermined level.

6. The method of claim 1 wherein the culture vessel can accommodate the cell-culture medium volume between 20 ml and 10 liters without substantially changing the bioreactor dynamics.

7. The method of claim 1, wherein said seeding of the cells in the culture vessel comprises aseptically transferring the cells to the culture vessel.

8. The method of claim 1, wherein said seeding of the cells in the culture vessel comprises automatically transferring the cells to the culture vessel.

9. The method of claim 1, wherein said seeding of the cells comprises aseptically and automatically transferring the cells to the culture vessel.

10. The method of claim 9, wherein said seeding of the cells to the culture vessel comprises transferring the cells to the culture vessel from a cryopreserved cell-stock.

11. The method of claim 1, wherein the cells are selected from the group consisting of bacterial cells, plant cells, fungal cells, insect cells, viruses, animal cells, mammalian cells, stem cells and combinations thereof.

12. The method of claim 1, wherein the bioreactor is a multi-scale bioreactor.

13. The method of claim 1, wherein the bioreactor is configured to maintain a constant temperature during the seeding and culturing of the cells.

14. The method of claim 1, wherein the bioreactor is configured to maintain a constant pH during the seeding and culturing of the cells.

15. The method of claim 1, wherein the bioreactor is configured to maintain a constant dissolved oxygen during the seeding and culturing of the cells.

16. The method of claim 1, further comprising controlling a gas transfer within the culture vessel.

17. The method of claim 1, wherein the culture vessel further comprises one or more impellers for agitating the cell-culture medium.

18. The method of claim 1, further comprising providing a temperature feedback control for the cell-culture medium using one or more temperature sensors.

19. The method of claim 1, wherein the cells are selected from the group consisting of suspension cells, adherent cells, non-adherent cells, and combinations thereof.

* * * * *